US010808272B2

(12) United States Patent
Chang et al.

(10) Patent No.: US 10,808,272 B2
(45) Date of Patent: Oct. 20, 2020

(54) METHOD FOR PREPARING ANTIBODY THROUGH REGULATION OF SUGAR CONTENT OF ANTIBODY

(71) Applicant: Prestige Biopharma PTE. LTD., Singapore (SG)

(72) Inventors: Jae Young Chang, Daejeon (KR); Eun Ho Hwang, Daejeon (KR); Yong Jin Kim, Gyuam-myeon (KR); Won Kyum Kim, Daejeon (KR); Sang Kyung Park, Daejeon (KR); Jun Yong Park, Incheon (KR); Kyo Eun Ahn, Seoul (KR); Yong Ho Ahn, Daejeon (KR); Ji Yong Yoon, Daejeon (KR); Jung Woo Lee, Daejeon (KR)

(73) Assignee: Prestige Biopharma PTE. LTD., Singapore (SG)

( * ) Notice: Subject to any disclaimer, the term of this patent is extended or adjusted under 35 U.S.C. 154(b) by 84 days.

(21) Appl. No.: 15/300,710

(22) PCT Filed: Apr. 2, 2015

(86) PCT No.: PCT/KR2015/003310
§ 371 (c)(1),
(2) Date: Sep. 29, 2016

(87) PCT Pub. No.: WO2015/152658
PCT Pub. Date: Oct. 8, 2015

(65) Prior Publication Data
US 2017/0107551 A1 Apr. 20, 2017

(30) Foreign Application Priority Data
Apr. 2, 2014 (KR) .................. 10-2014-0039307

(51) Int. Cl.
C07K 16/28 (2006.01)
C07K 16/18 (2006.01)
A61K 39/395 (2006.01)
C12P 21/08 (2006.01)
C12P 21/00 (2006.01)
C07K 16/00 (2006.01)
C07K 16/32 (2006.01)

(52) U.S. Cl.
CPC ........ C12P 21/005 (2013.01); A61K 39/3955 (2013.01); A61K 39/39591 (2013.01); C07K 16/00 (2013.01); C07K 16/2863 (2013.01); C07K 16/32 (2013.01); C07K 2317/14 (2013.01); C07K 2317/24 (2013.01); C07K 2317/41 (2013.01); C07K 2317/732 (2013.01); C07K 2317/92 (2013.01)

(58) Field of Classification Search
None
See application file for complete search history.

(56) References Cited

U.S. PATENT DOCUMENTS

| 7,439,043 B2 | 10/2008 | Defrees et al. |
| 2007/0092521 A1 | 4/2007 | McPherson et al. |
| 2012/0115187 A1* | 5/2012 | Retallack ............... C12N 15/65 435/69.1 |

(Continued)

FOREIGN PATENT DOCUMENTS

| CN | 103080130 A | 5/2013 | |
| EP | 2468869 A1 * | 6/2012 | ........... C12N 15/625 |
| JP | 08-336389 A | 12/1996 | |

(Continued)

OTHER PUBLICATIONS

Rosano et al., Front Microbiol., 2014, vol. 5, article 172, pp. 1-17.*

(Continued)

*Primary Examiner* — Xiaozhen Xie
(74) *Attorney, Agent, or Firm* — John P. White; Gary J. Gershik; Cooper & Dunham LLP

(57) ABSTRACT

Provided are a method of preparing an antibody with a regulated, sugar chain content, the method including the step of culturing antibody-expressing cells in a medium including glycerol as an additive for regulating the antibody sugar chain content, a method of preparing a high-quality population of antibodies by regulating the sugar content of the antibody to a desired content, and a population of antibodies prepared by the method. Further, provided is a method of regulating the antibody sugar chain content, the method including the step of culturing antibody-expressing cells in a medium including glycerol as an additive for regulating the antibody sugar chain content. Furthermore, provided is a medium composition, for regulating the antibody sugar chain content, the medium composition including glycerol as an additive for regulating the antibody sugar chain content. The preparation method of antibodies according to the present invention may be used to prepare a desired high-quality population of antibodies by regulating the sugar chain content of the antibody. Further, in terms of the development of biosimilars, the method of the present, invention may be used to regulate the sugar chain, content of antibodies, thereby preparing antibodies having high equivalence to a control drug. Since the sugar chain content may be regulated by a medium composition, the regulation method is easy and efficient in terms of time and cost, and therefore, widely applied to the fields of antibody preparation.

12 Claims, 35 Drawing Sheets

(56) References Cited

U.S. PATENT DOCUMENTS

| | | | |
|---|---|---|---|
| 2012/0276631 A1 | 11/2012 | Bengea et al. | |
| 2013/0071390 A1* | 3/2013 | Stadheim | C07K 16/00 424/133.1 |

FOREIGN PATENT DOCUMENTS

| | | |
|---|---|---|
| JP | 2007-535913 A | 12/2007 |
| JP | 4102752 B2 | 6/2008 |
| JP | 4368530 B2 | 11/2009 |
| JP | 2013-529908 A | 7/2013 |
| KR | 10-2013-0057959 A | 6/2013 |
| KR | 10-2013-0102936 A | 9/2013 |
| WO | WO 2012/115904 A2 | 8/2012 |
| WO | WO 2012/149197 A2 | 11/2012 |

OTHER PUBLICATIONS

Christel et al., Protocol Exchange (2015) doi:10.1038/protex.2015.032 (2 pages).*

Office Action dated Aug. 30, 2017 in connection with Japanese Patent Application No. JP 2016-559960 including English language machine translation.

Gramer, Michael J., et al, "Modulation of Antibody Galactosylation Through Feeding of Uridine, Manganese Chloride, and Galactose", Biotechnology and Bioengineering, 2011, vol. 108, pp. 1591-1602.

Grainer, Rhian K. and James, David C., "CHO Cell Line Specific Prediction and Control of Recombinant Monoclonal Antibody N-Glycosylation", Biotechnology and Bioengineering, 2013, vol. 110, pp. 2970-2983.

Office Action dated Jan. 16, 2018 in connection with Japanese Patent Application No. JP 2016-559960 including an English language machine translation obtained from the USPTO Global Dossier for JP 2016-559960.

Chinese Patent Application Publication No. CN103080130 A, published May 1, 2013 to Merck Sharp & Dohme Corp, including an English language translation of the abstract.

International Search Report in connection with PCT International Application No. PCT/KR2015/003310, (dated Jul. 20, 2015).

Sawa, et al., "Glycoproteomic probes for fluorescent imaging of fucosylated glycans in vivo", PNAS, 2006, vol. 103(33):12371-12376.

Yamane-Ohnuki et al., "Establishment of FUT8 knockout Chinese hamster ovary cells: an ideal host cell line for producing completely defucosylated antibodies with enhanced antibody-dependent cellular cytotoxicity", Biotechnology and Bioengineering, 2004, vol. 87(5):614-622.

Hossler, et al., "Optimal and consistent protein glycosylation in mammalian cell culture", Glycobiology, 2009, vol. 19(9):936-949.

Yoshinobu, et al., "Fucose content of monoclonal antibodies can be controlled by culture medium osmolality for high antibody-dependent cellular cytotoxicity", Cytotechnology 2012, vol. 64(3):249-265.

Efren Pacis, et al., "Understanding the intracellular effect of enhanced nutrient feeding toward high titer antibody production process", Biotechnology and Bioengineering, 2011, vol. 108(5):1078-1088.

Office Action dated Jan. 22, 2020 by the European Patent Office in connection with counterpart European Patent Application No. 15 773 537.4.

Von Horsten H H et al, "Production of non-fucosylated antibodies by co-expression of heterologous GDP-6-deoxy-D-lyxo-4-hexulose reductase", Glycobiology, Oxford University Press, US, vol. 20, No. 12, Dec. 1, 2010 (Dec. 1, 2010), pp. 1607-1618.

Yoshinobu Konno et al., "Fucose content of monoclonal antibodies can be contro.lled by culture medium osmolality for high antibody-dependent cellular cytotoxicity", Cytotechnology., vol. 64, No. 3, May 1, 2012 (May 1, 2012), pp. 249-265.

Extended European search report in connection with European Patent Application No. EP 15 77 3537, (dated Feb. 28, 2017).

P. Hossler, et al., "Optimal and consistent protein glycosylation in mammalian cell culture", Glycobiology, Jun. 3, 2009, vol. 19, No. 9, pp. 936-949.

M. Rezaei, et al., "The effect of different media composition and temperatures on the production of recombinant human growth hormone by CHO cells", Research in Pharmaceutical Sciences, Jul. 2013; vol. 8, No. 3, pp. 211-217.

J. Rodriguez, et al., "Enhanced Production of Monomeric Interferon-β by CHO Cells through the Control of Culture Conditions" Biotechnological Progress, American Institute of Chemical Engineers, Jan. 1, 2005, vol. 21, No. 1, pp. 22-30, US.

Eiji Suzuki, et al., "A Nonfucosylated Anti-HER2 Antibody Augments Antibody-Dependent Cellular Cytotoxicity in Breast Cancer Patients", Clinical Cancer Research, The American Association for Cancer Research Mar. 15, 2007; vol. 13, No. 6, pp. 1875-1882, US.

* cited by examiner

[FIG. 1]
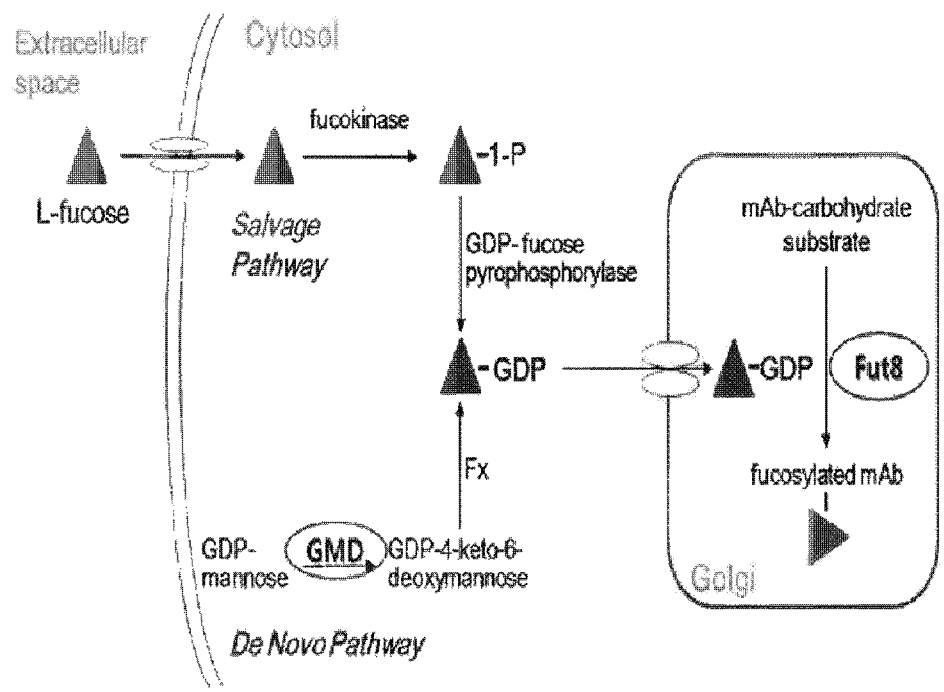

[FIG. 2]
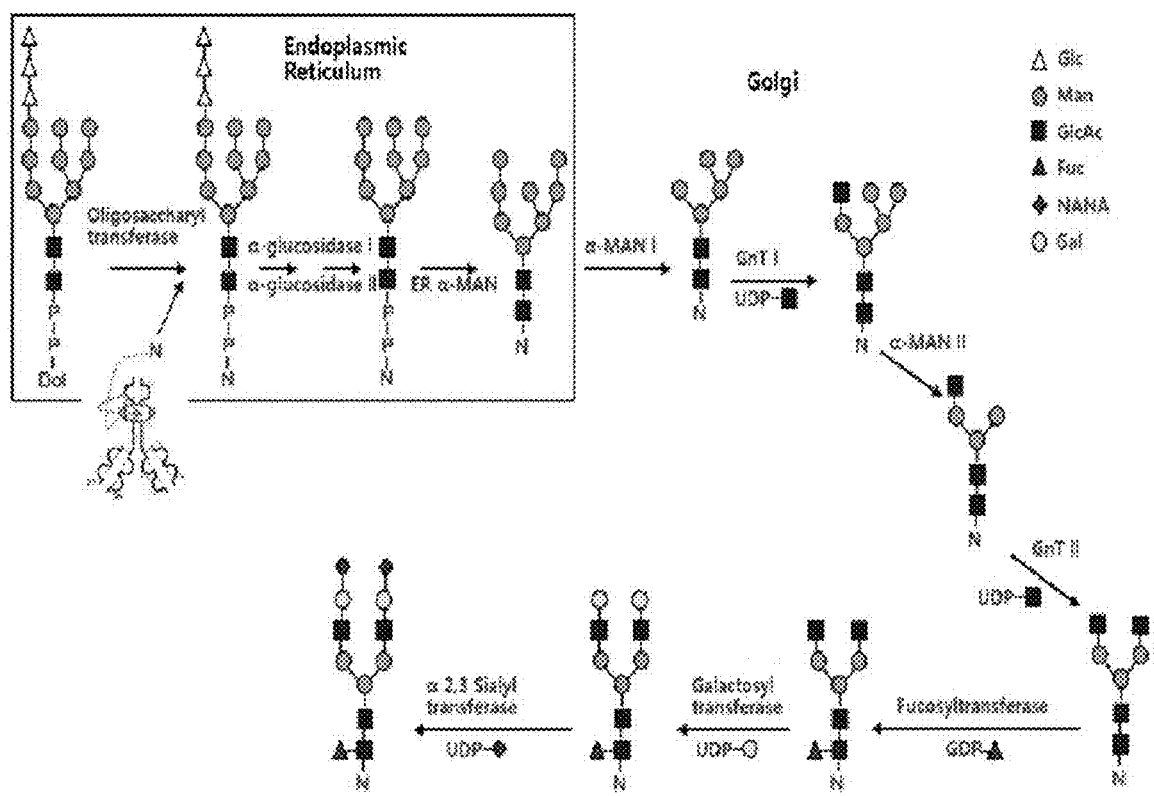
U.S Serial No.: 15/300,710
Applicant: Prestige Biopharma Pte. Ltd.
Filed (as §371): September 29, 2016
Exhibit A

[FIG. 3]
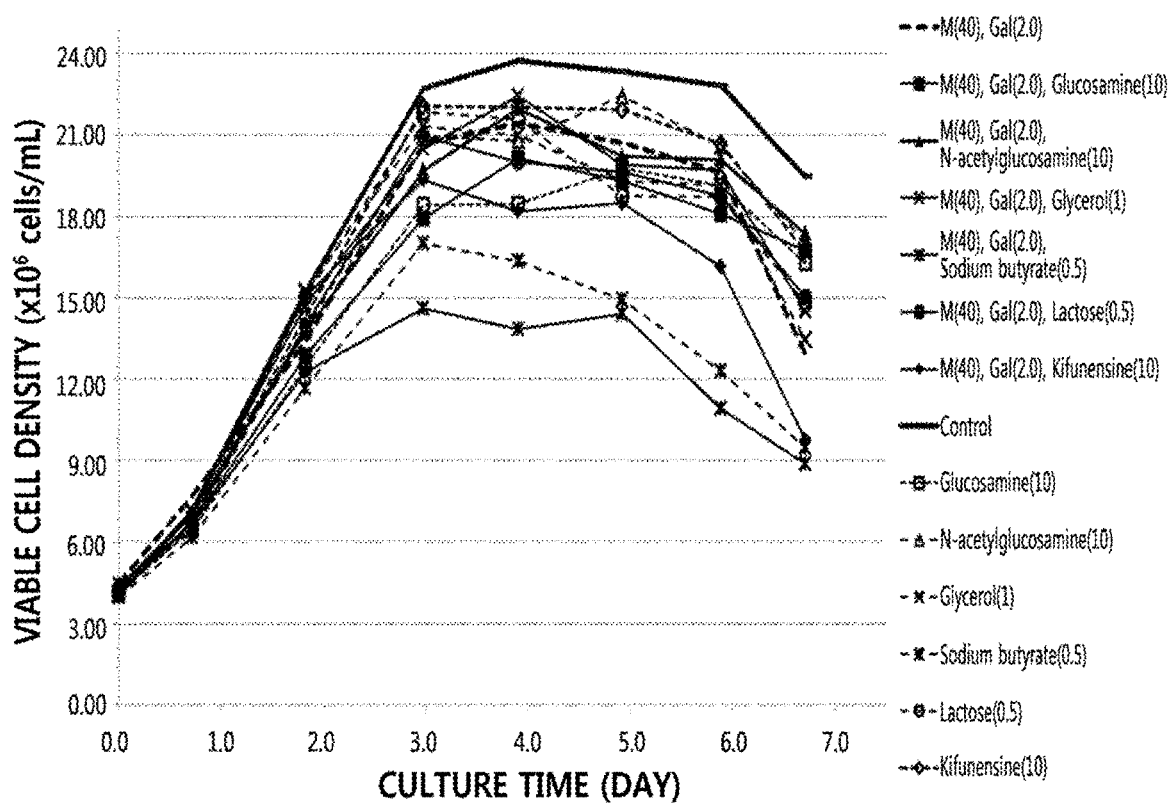

[FIG. 4]
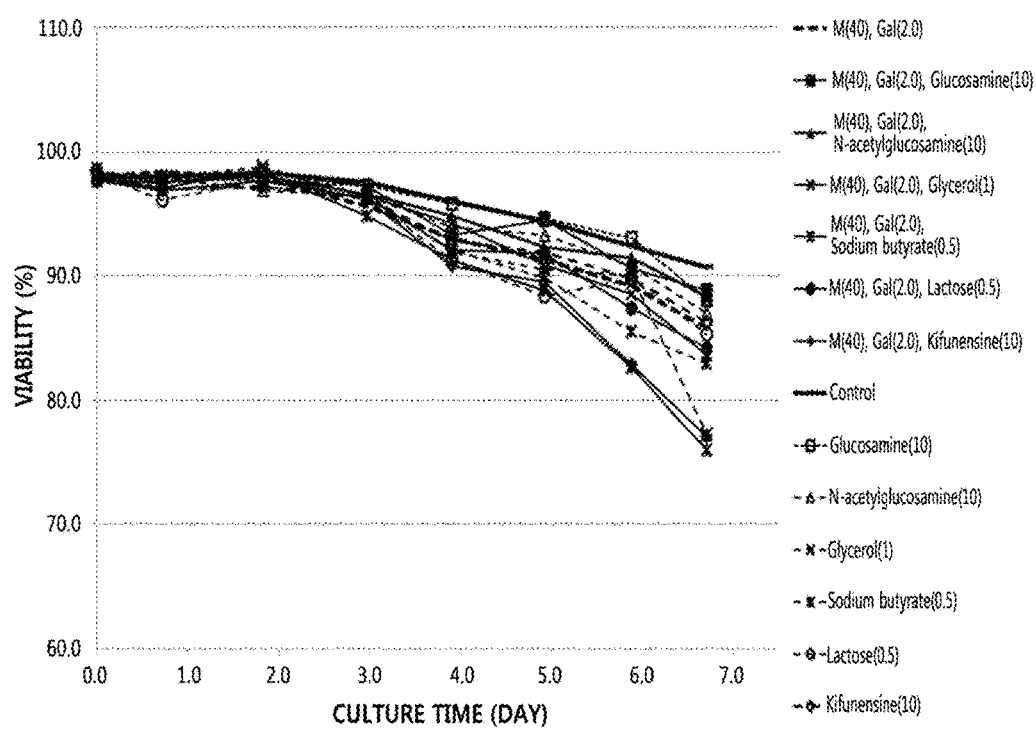

[FIG. 5]
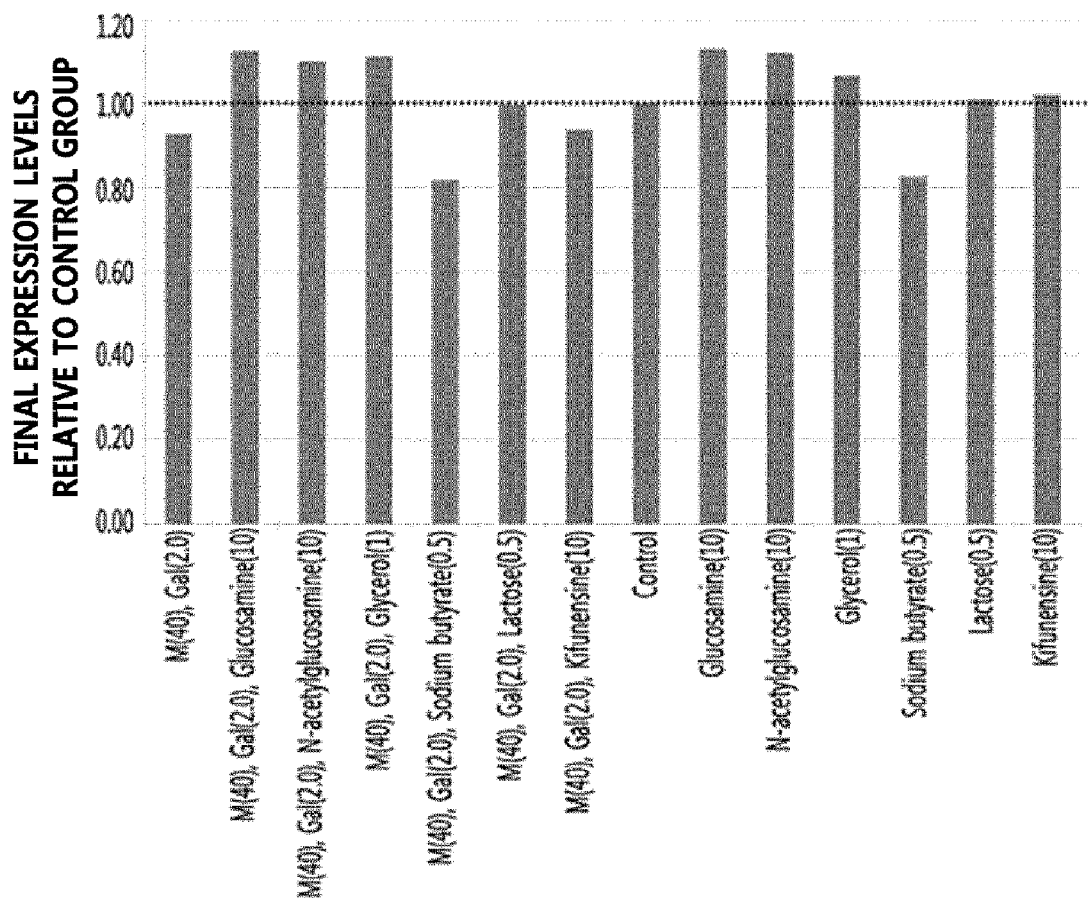

[FIG. 6]
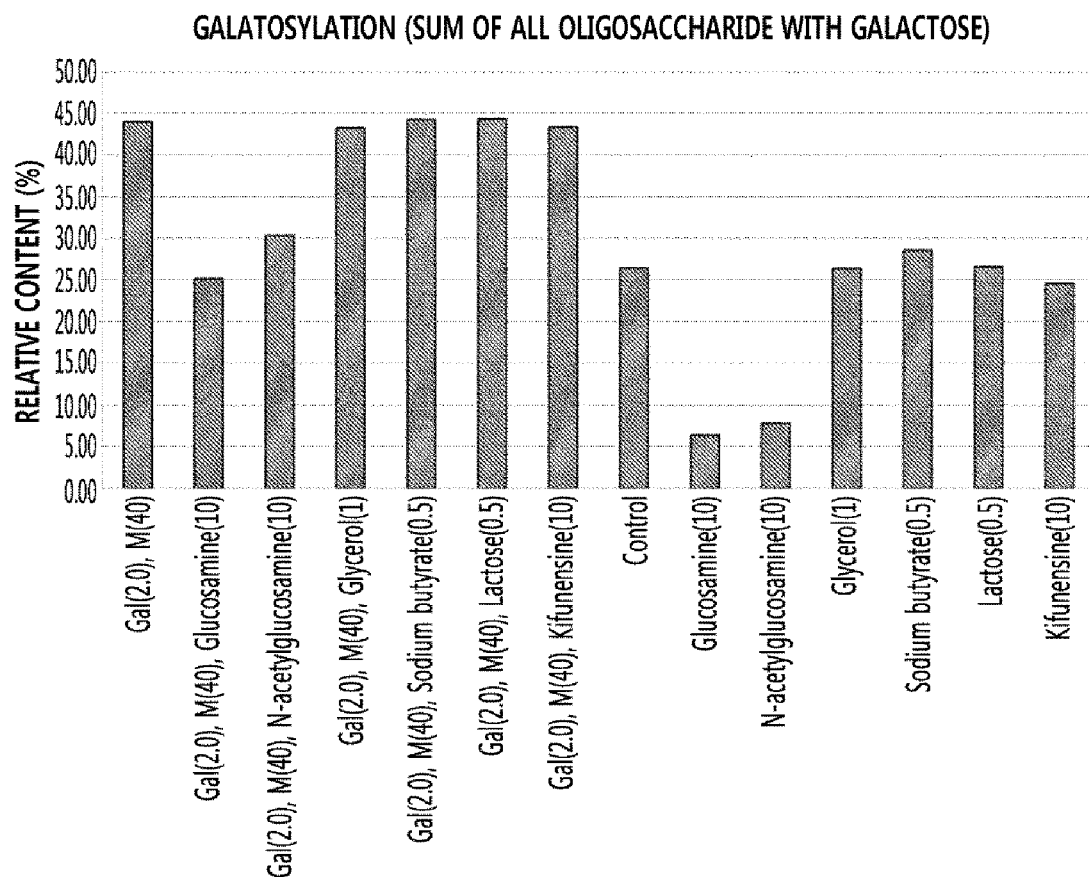

[FIG. 7]
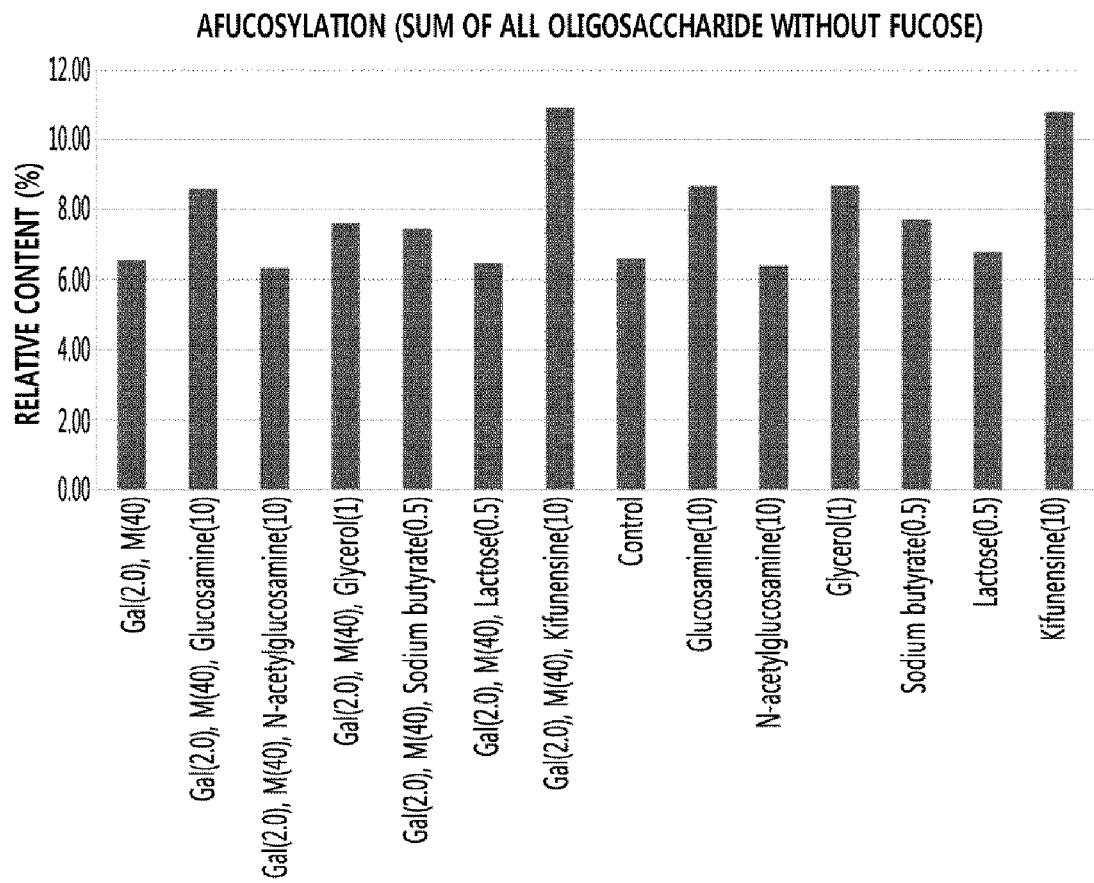

[FIG. 8]
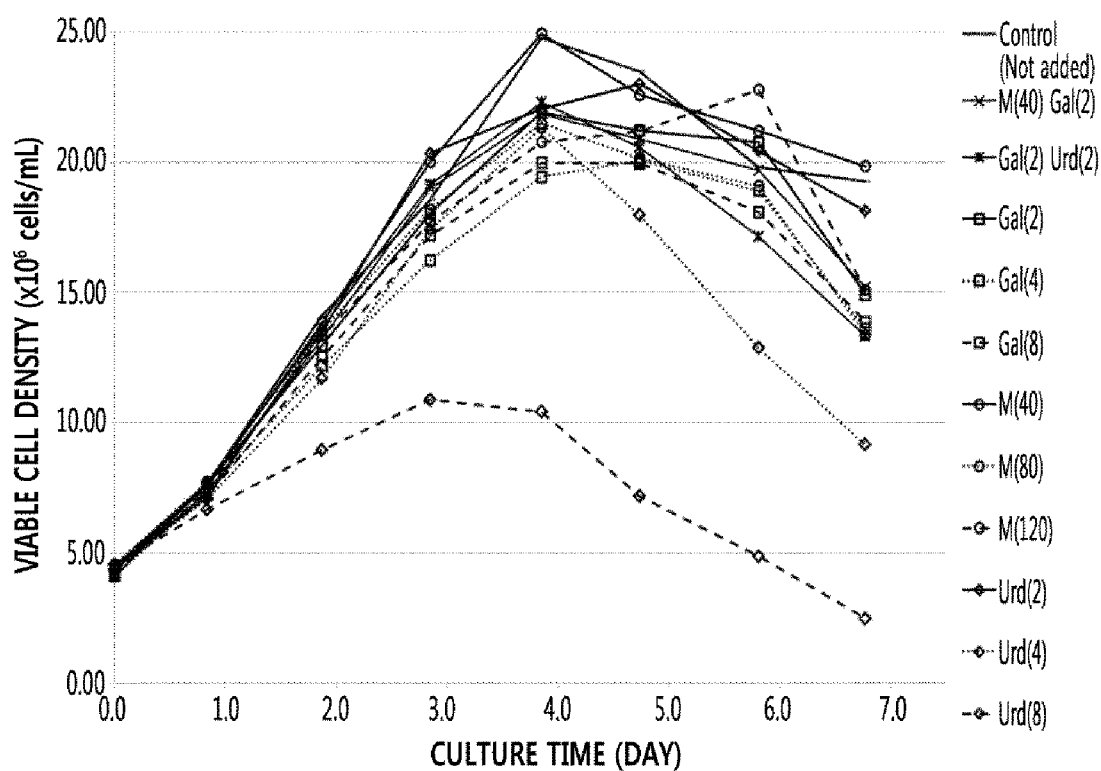

[FIG. 9]
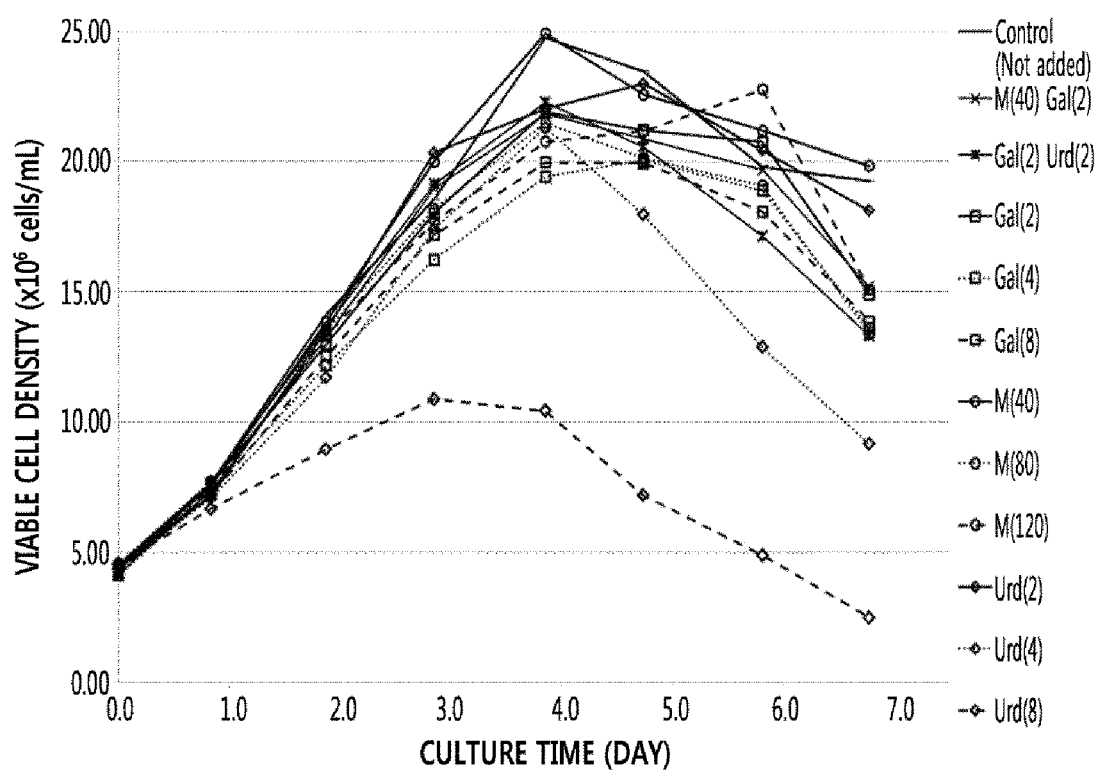

[FIG. 10]
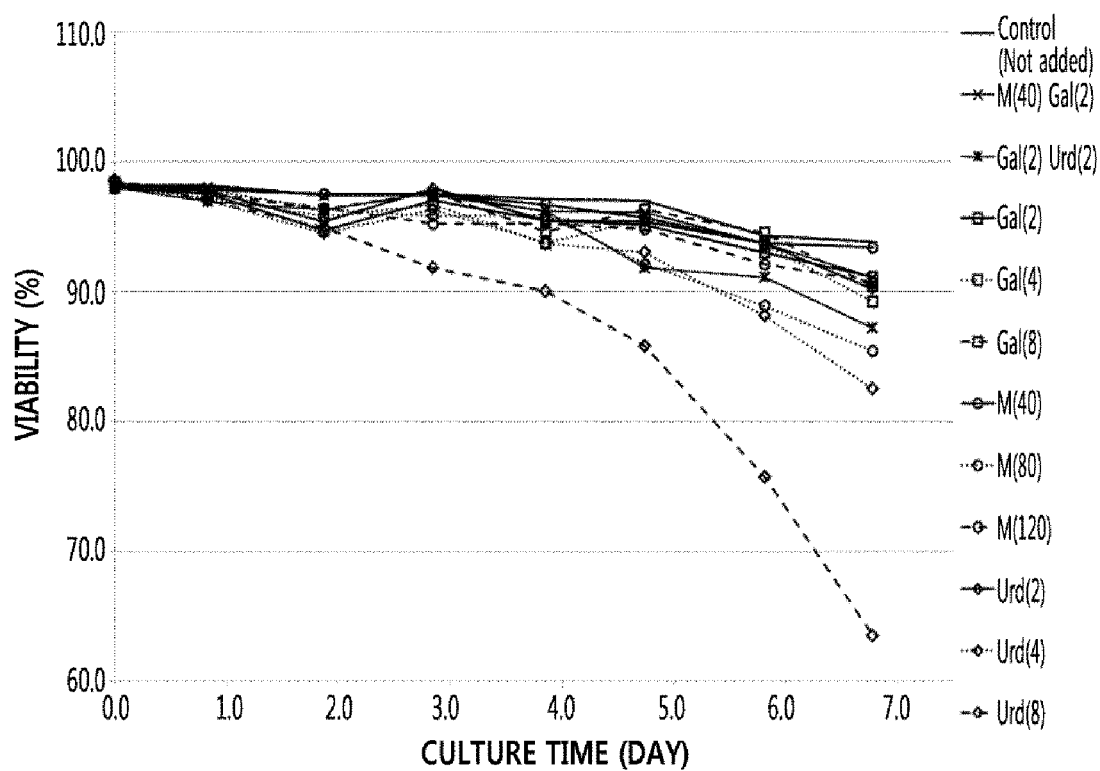

[FIG. 11]
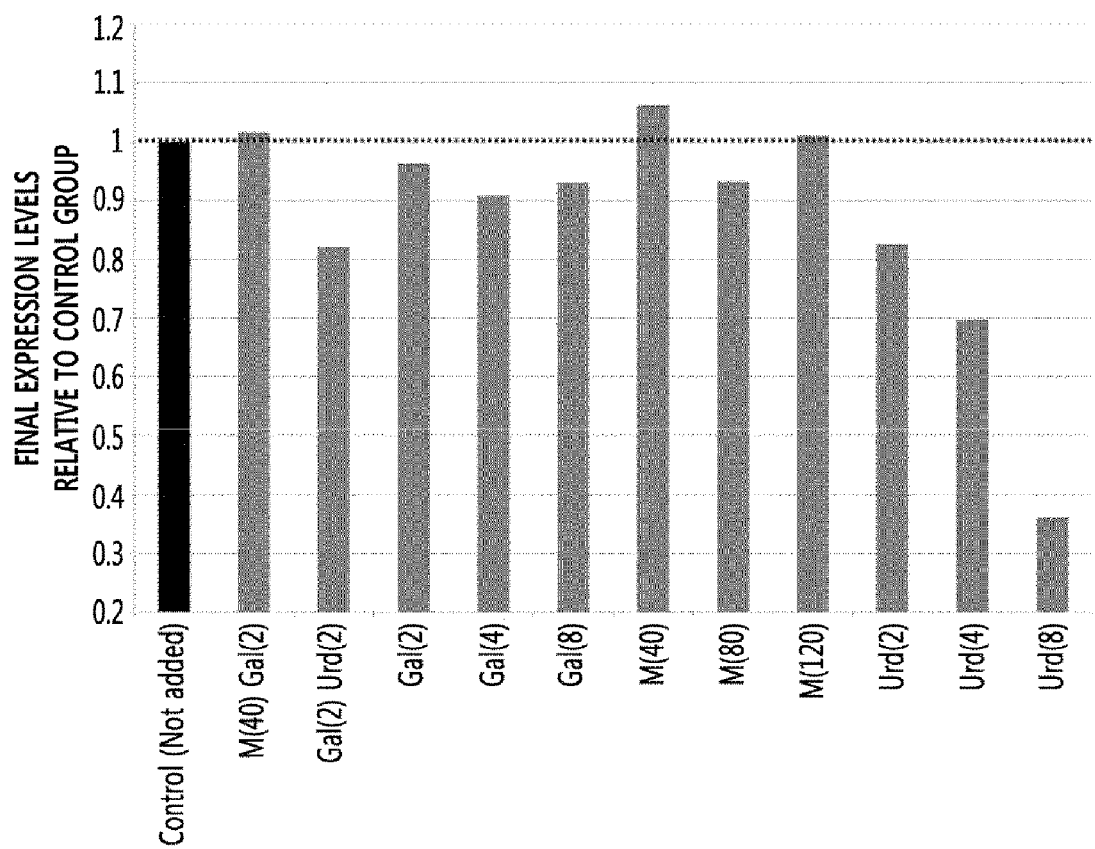

[FIG. 12]
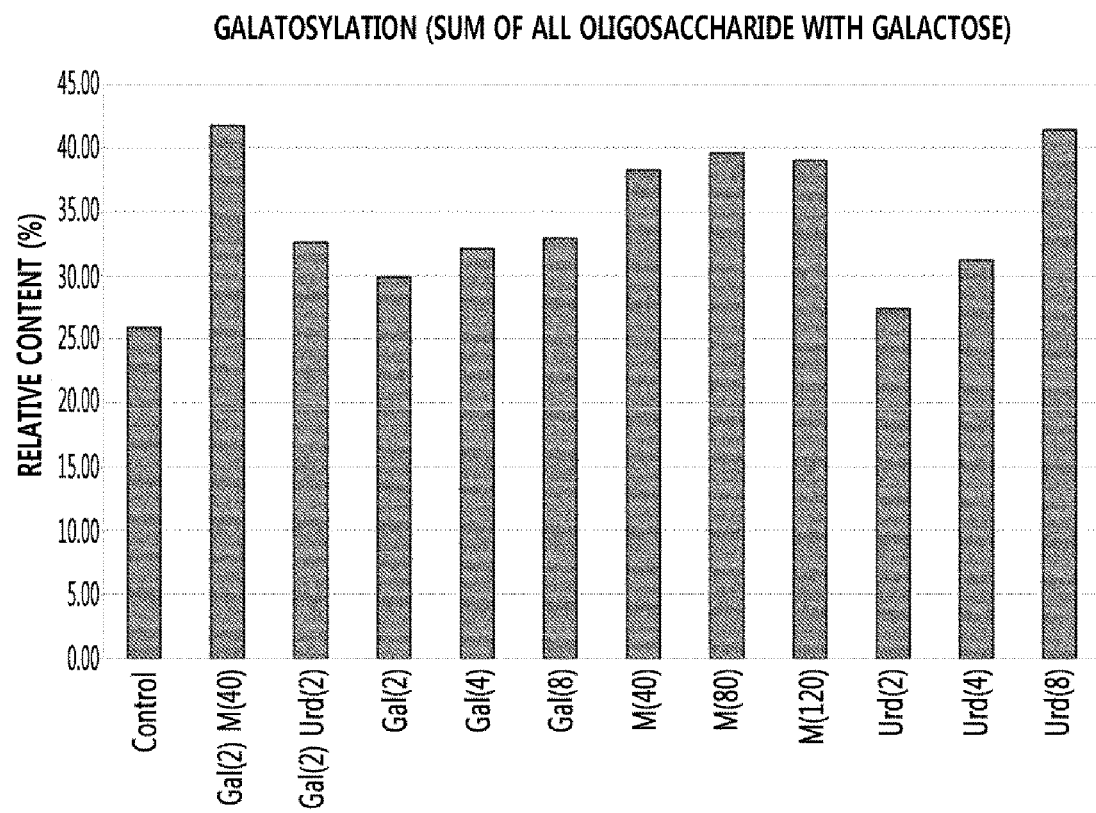

[FIG. 13]
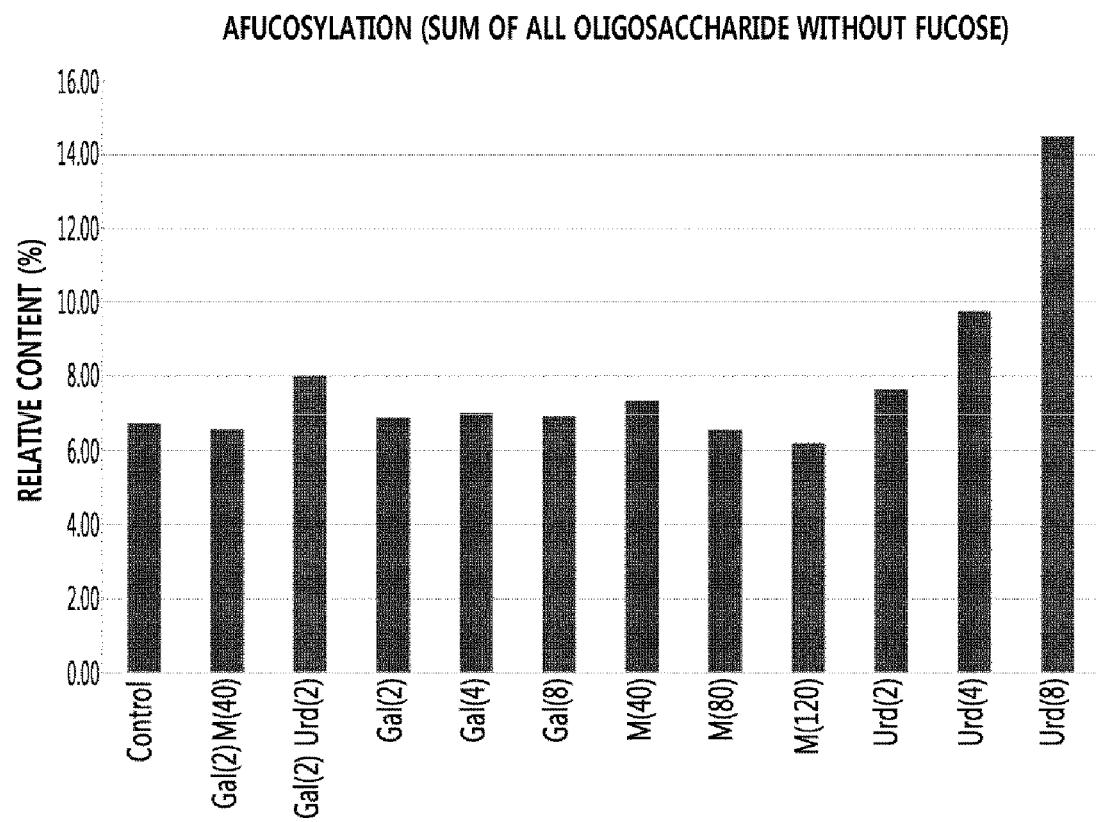

[FIG. 14]
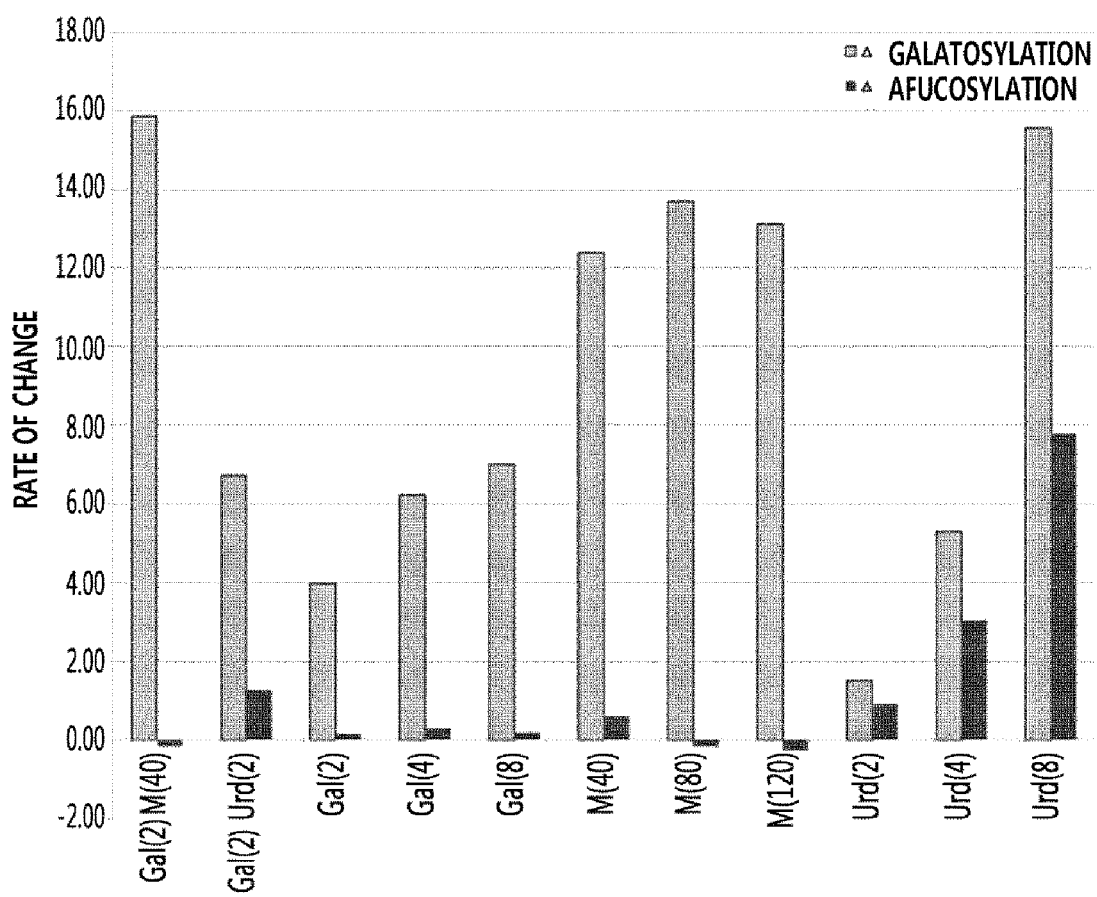

[FIG. 15]
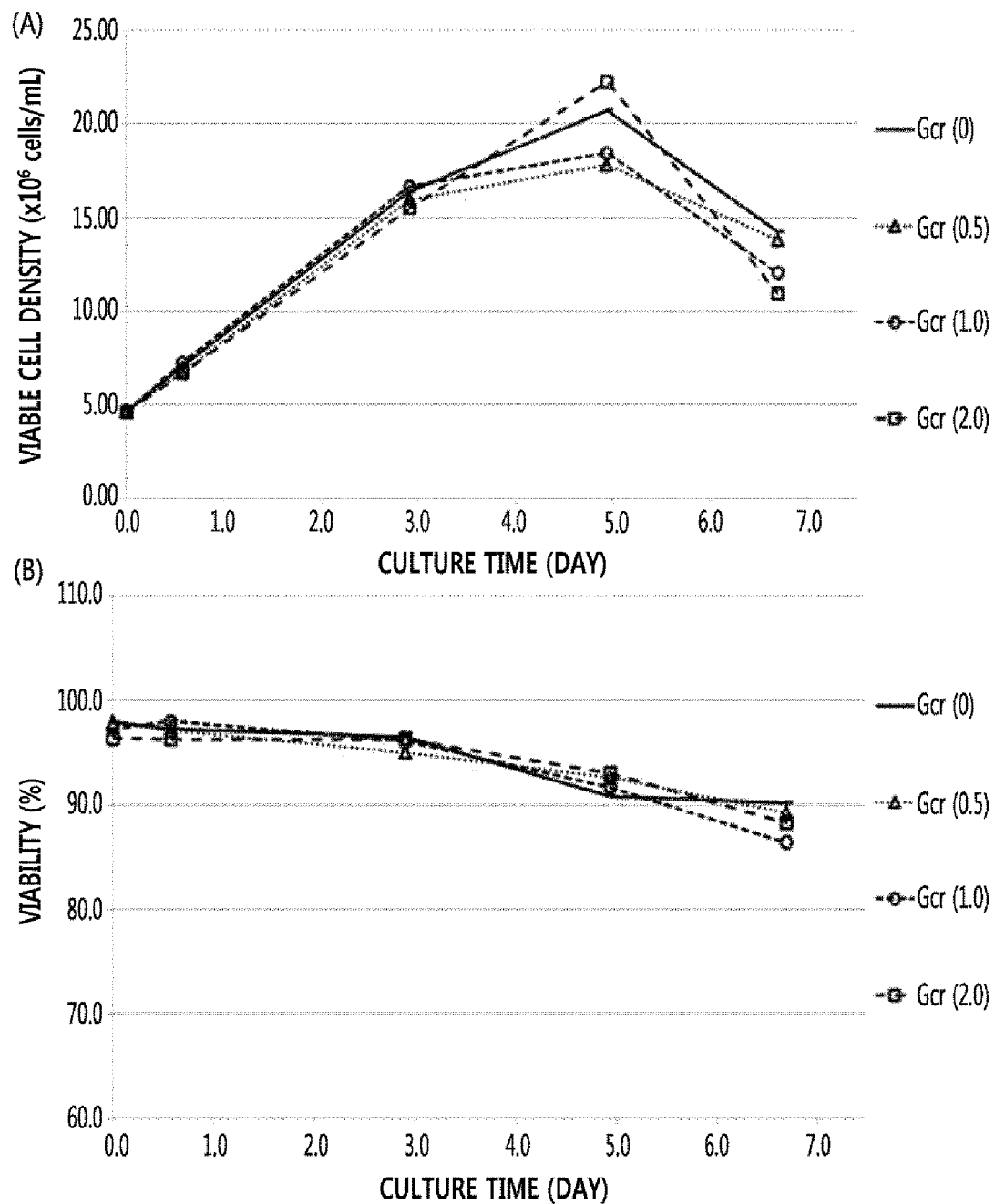

[FIG. 16]
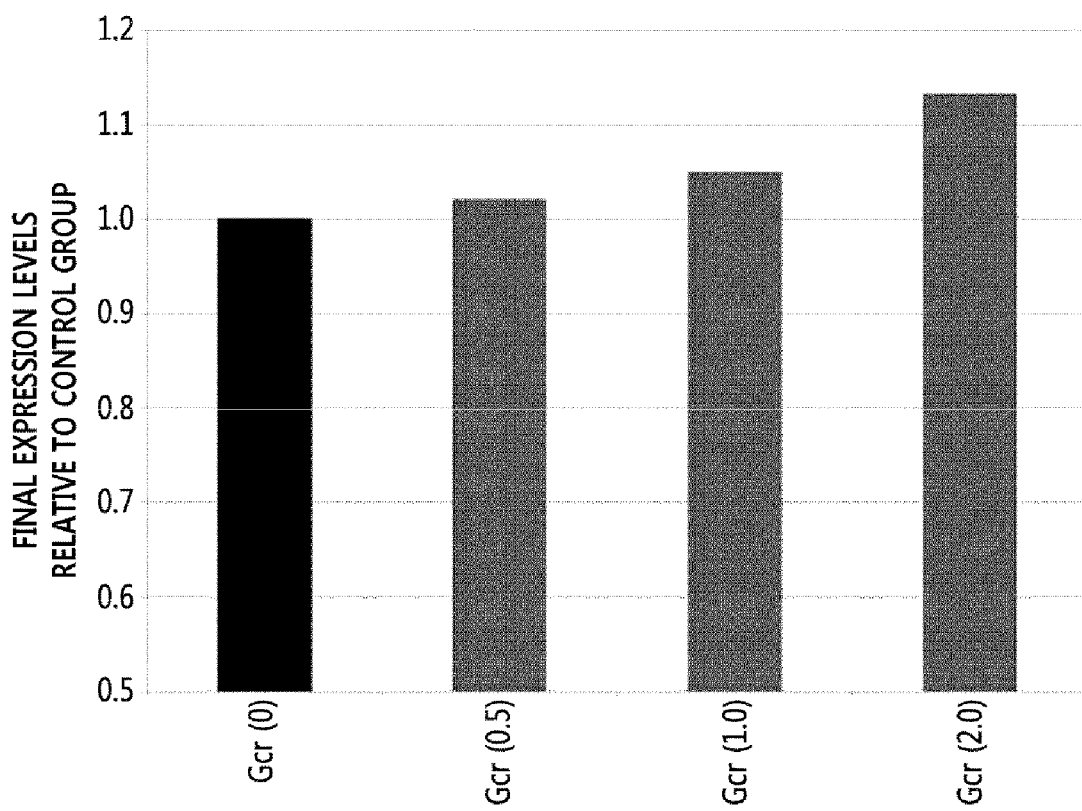

[FIG. 17]
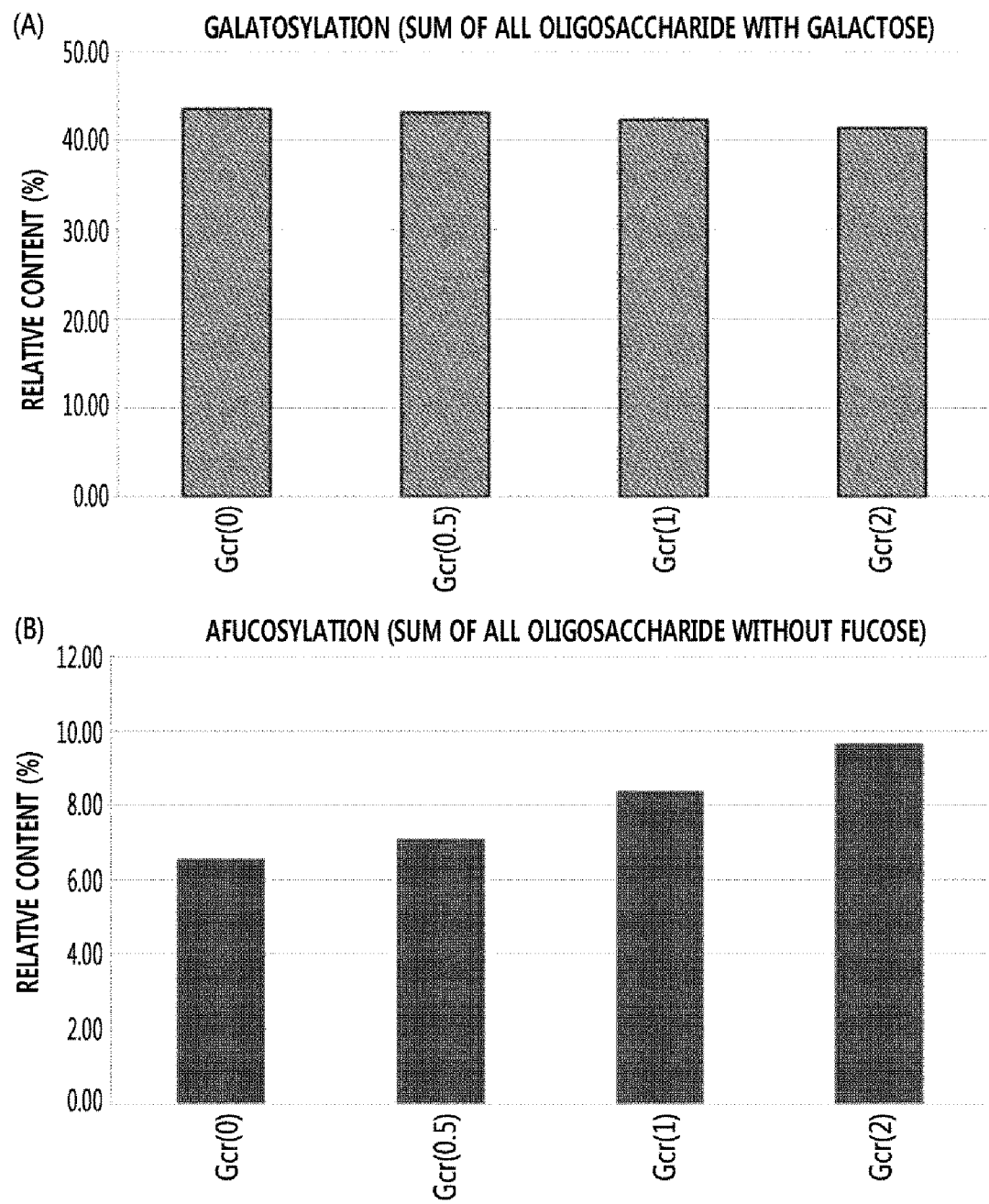

[FIG. 18]
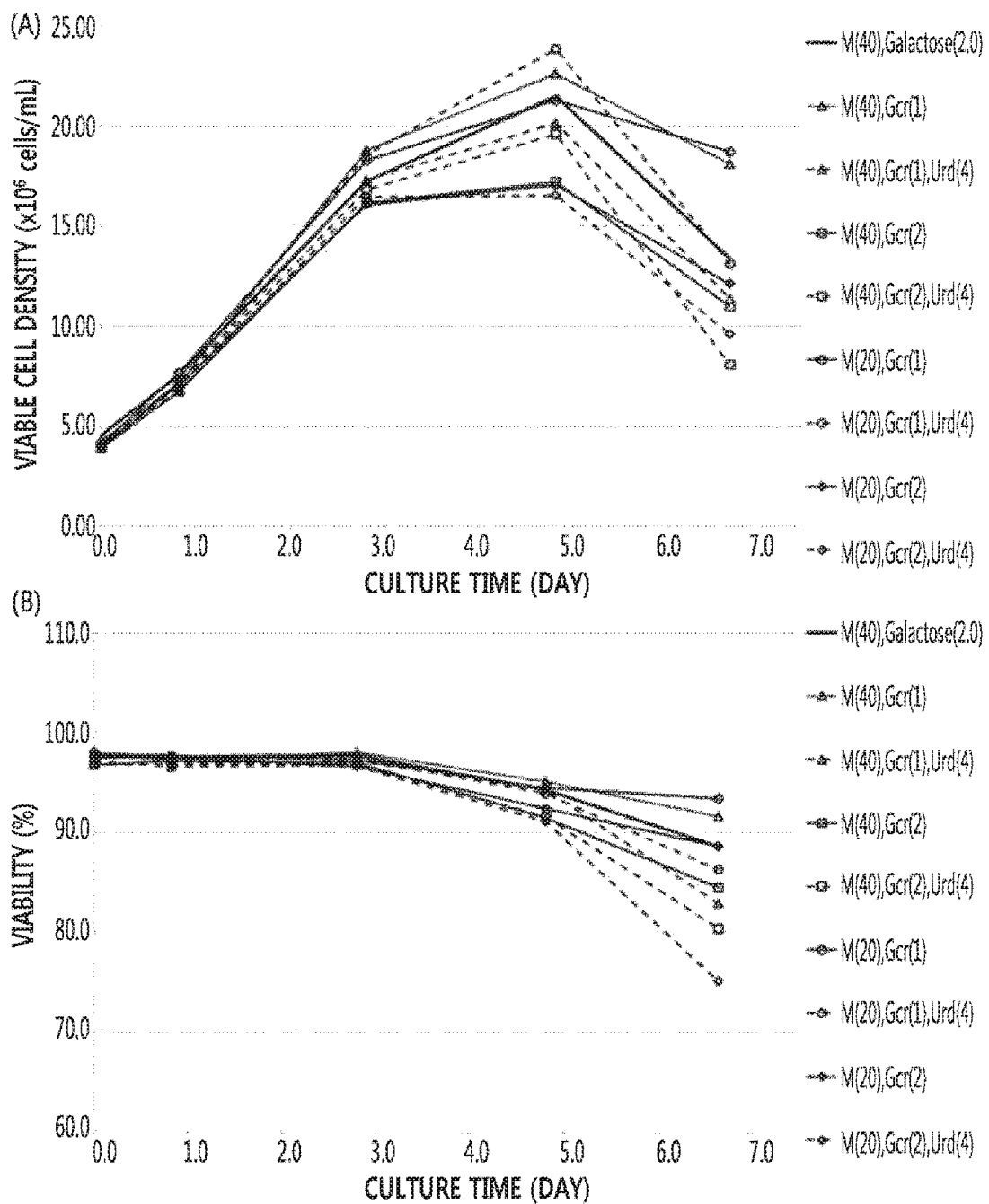

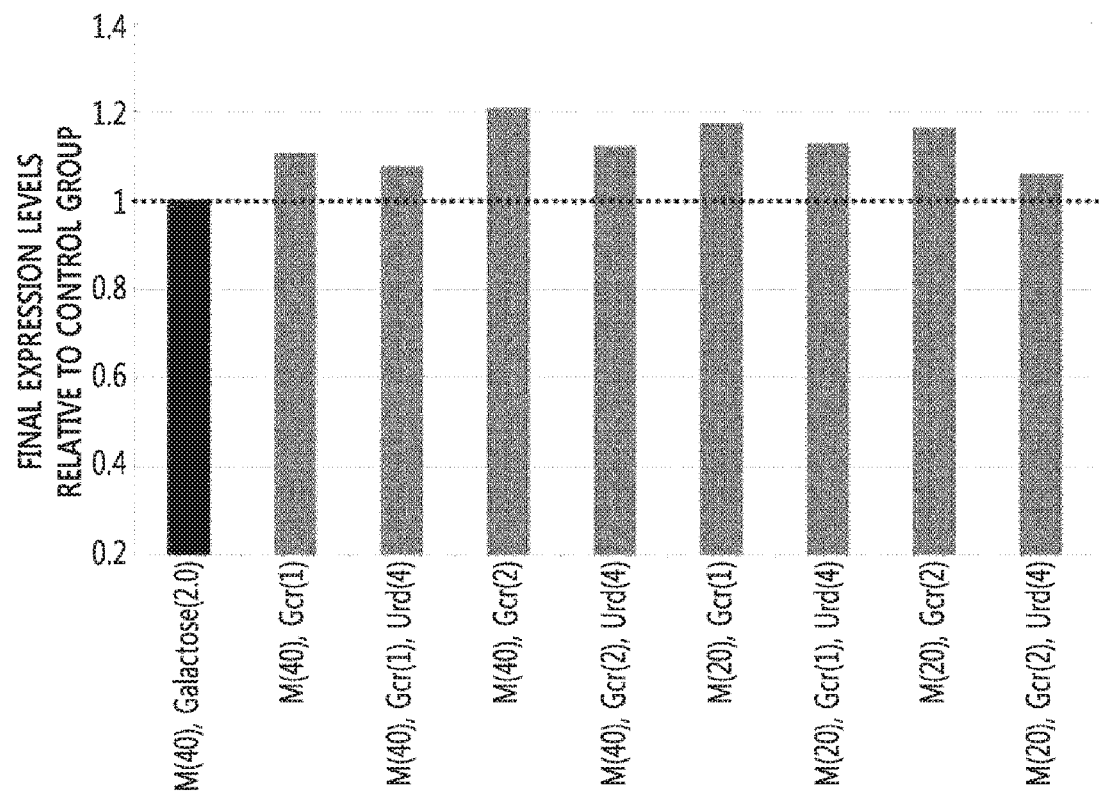
[FIG. 19]

[FIG. 20]
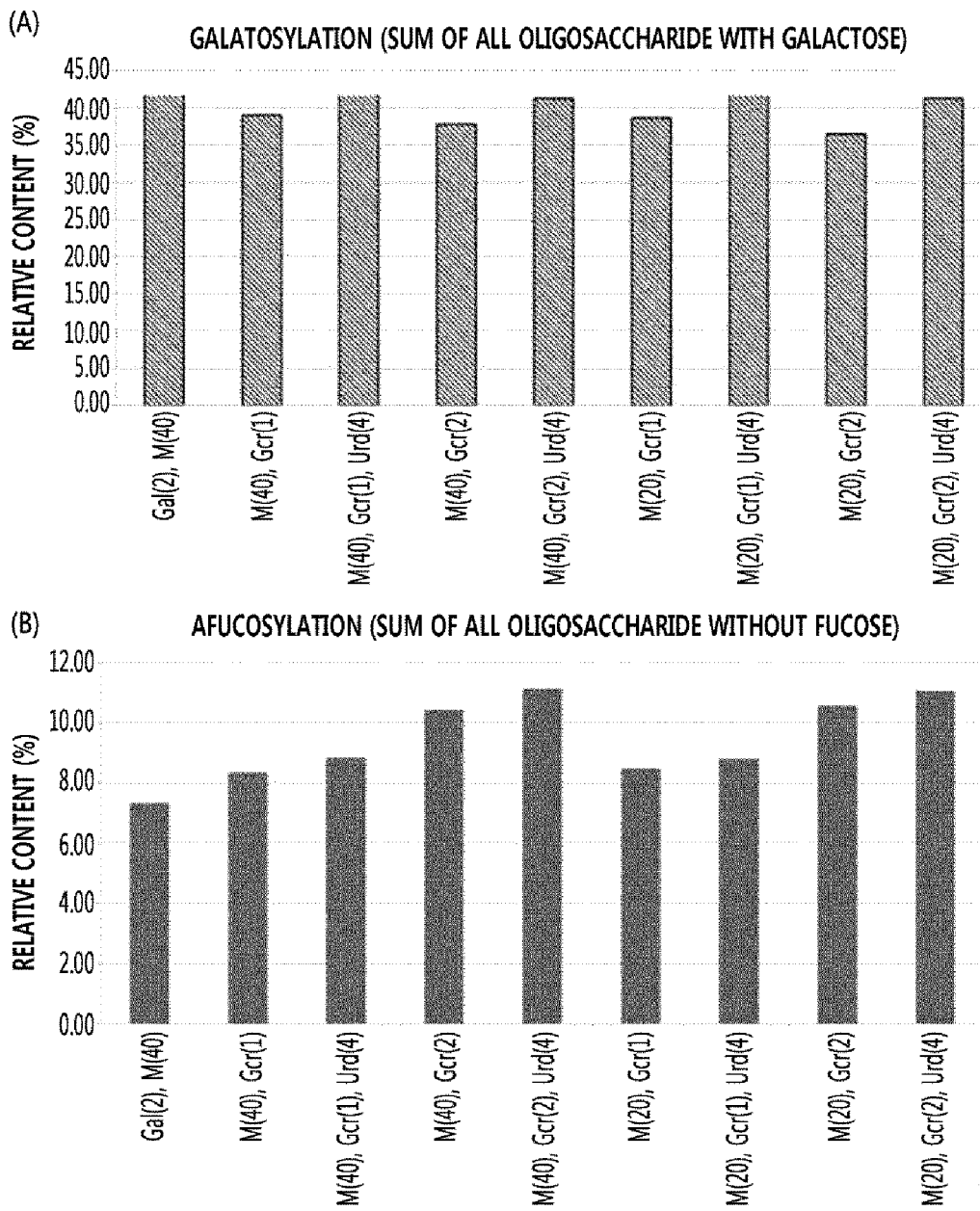

[FIG. 21]
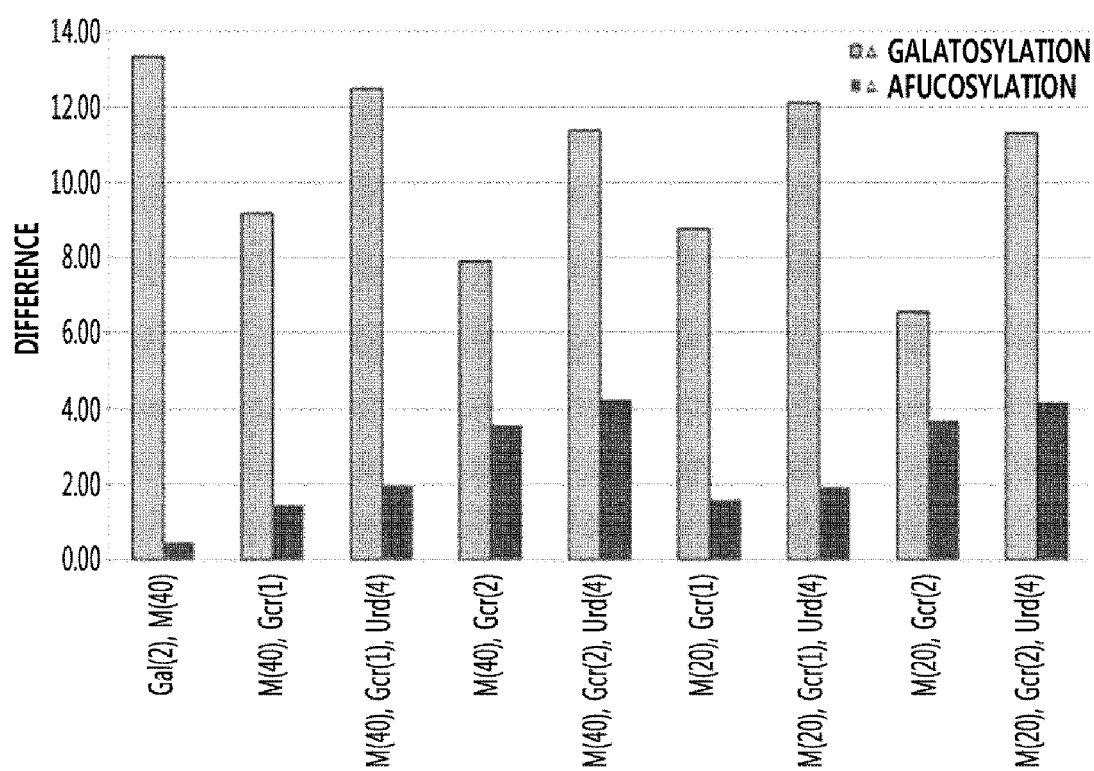

[FIG. 22]
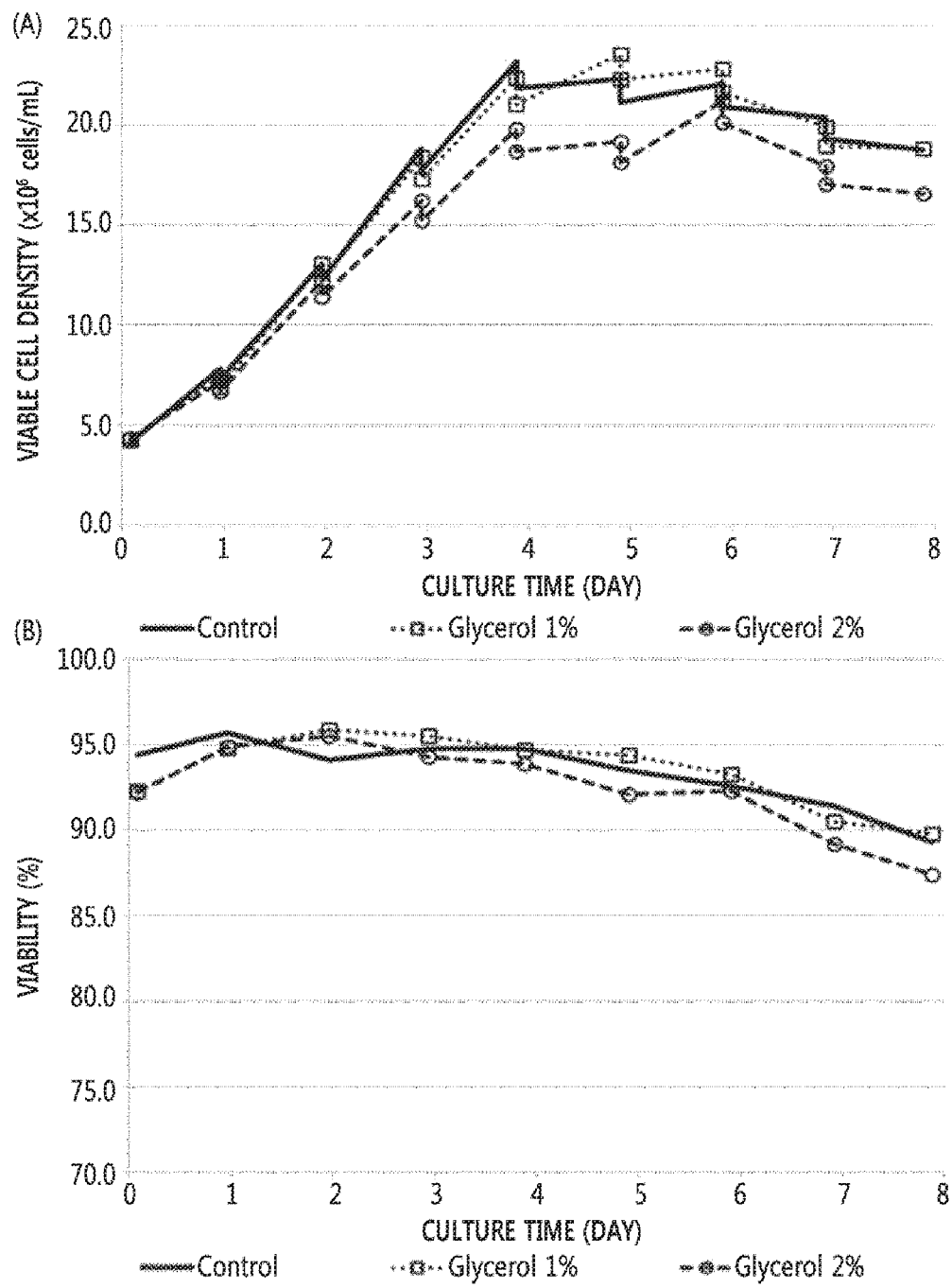

[FIG. 23]
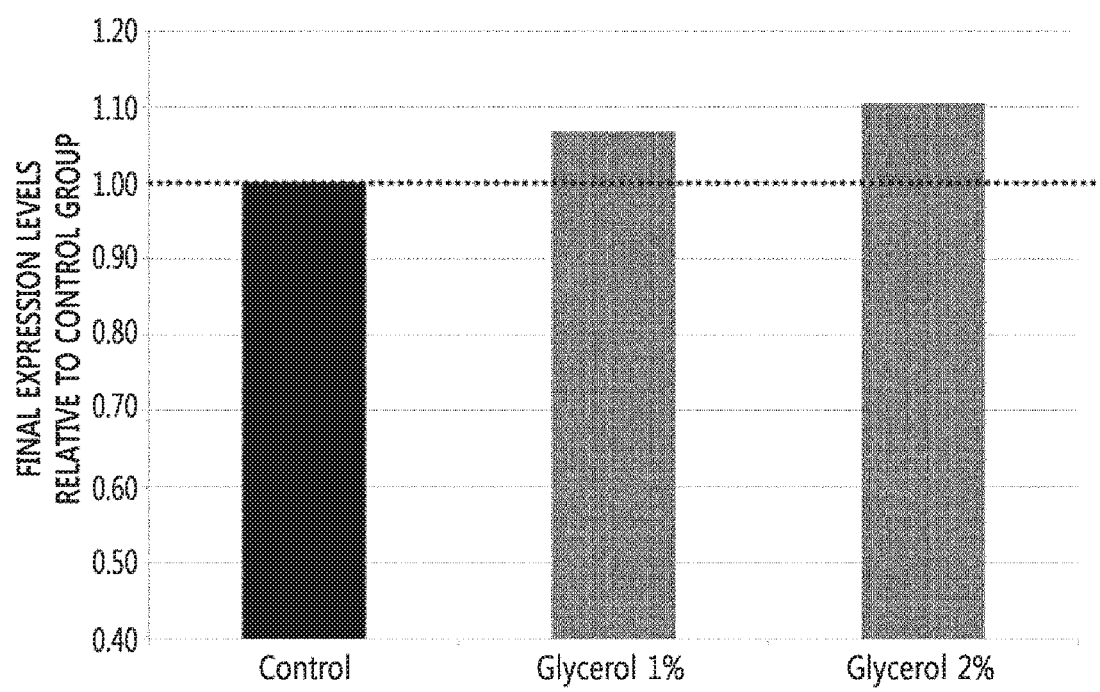

[FIG. 24]
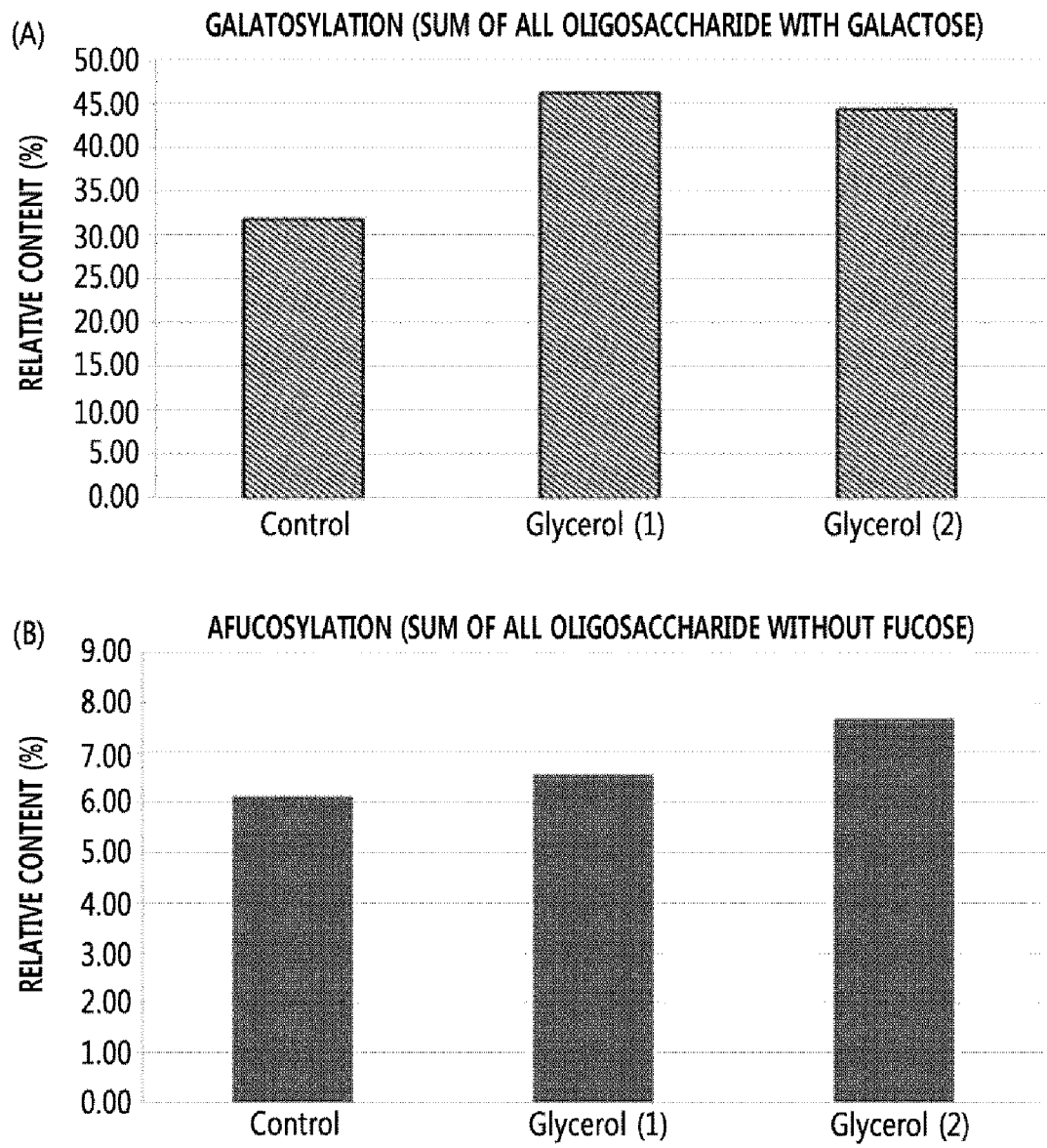

[FIG. 25]
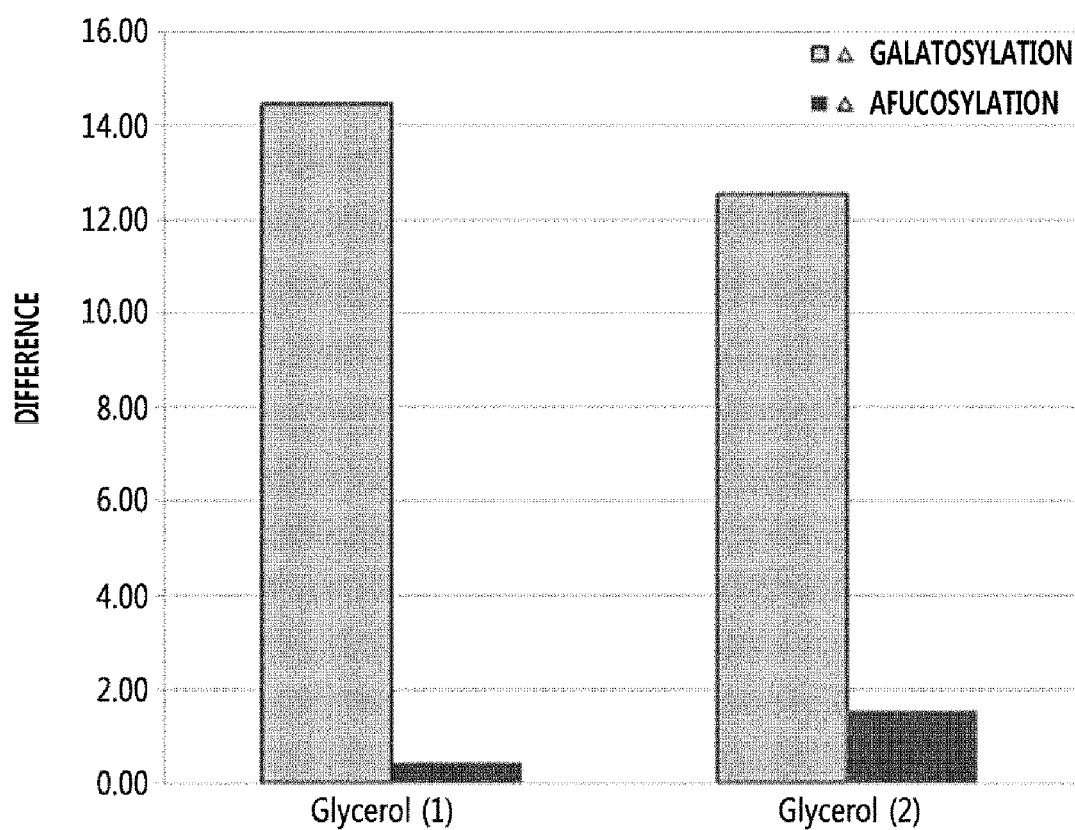

[FIG. 26]
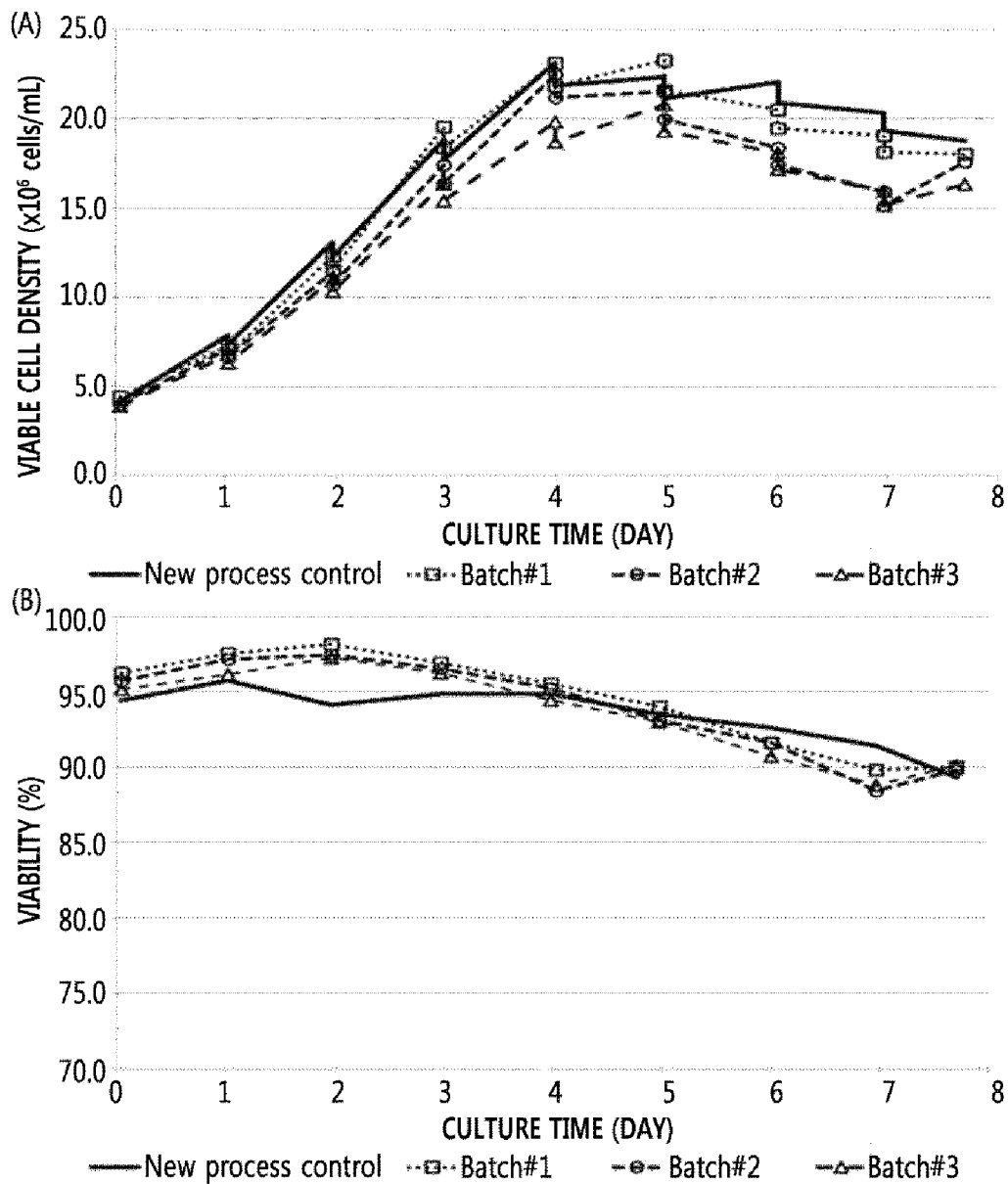

[FIG. 27]
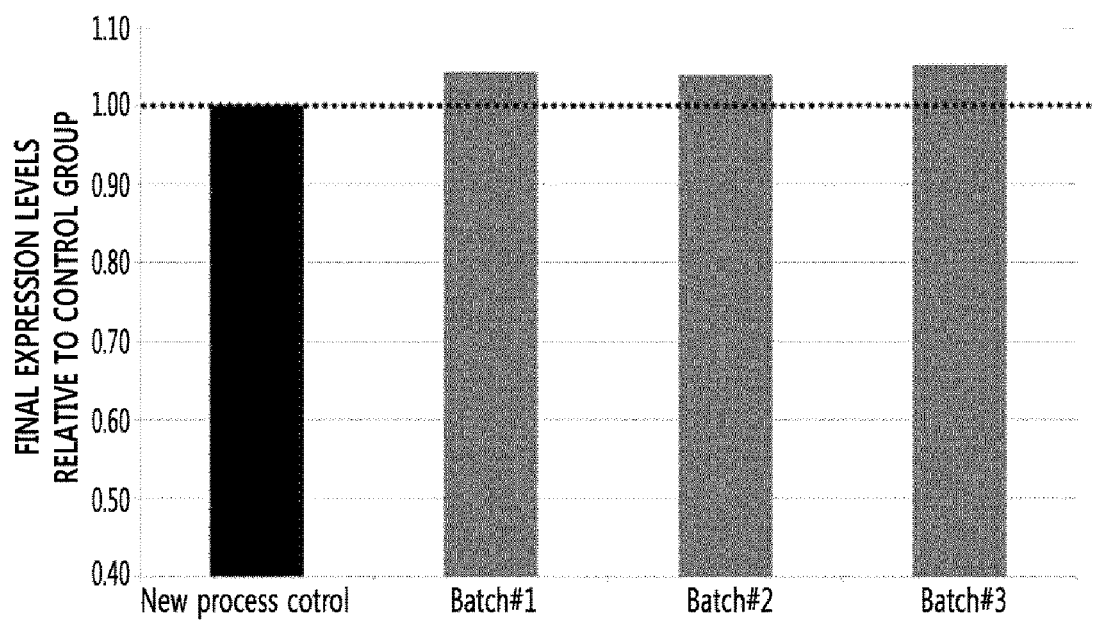

[FIG. 28]
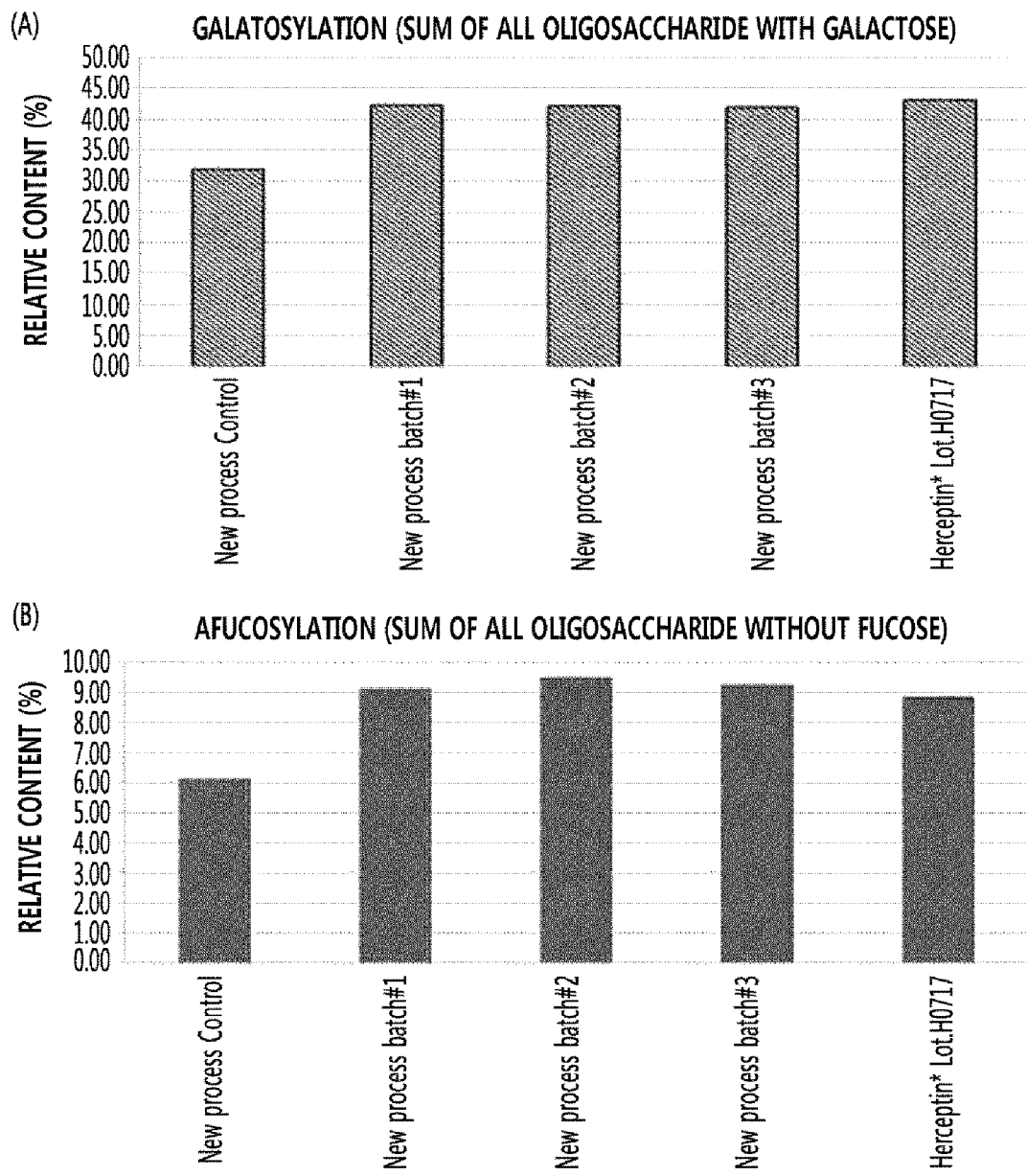

[FIG. 29]
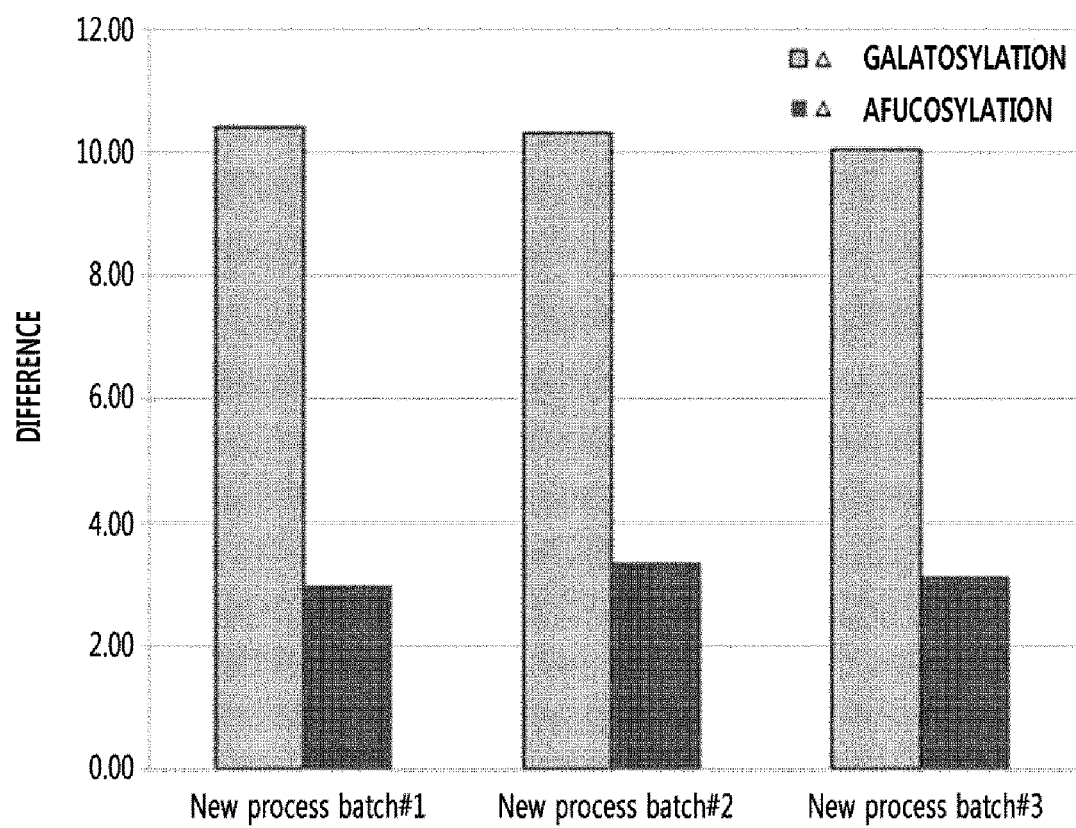

[FIG. 30]
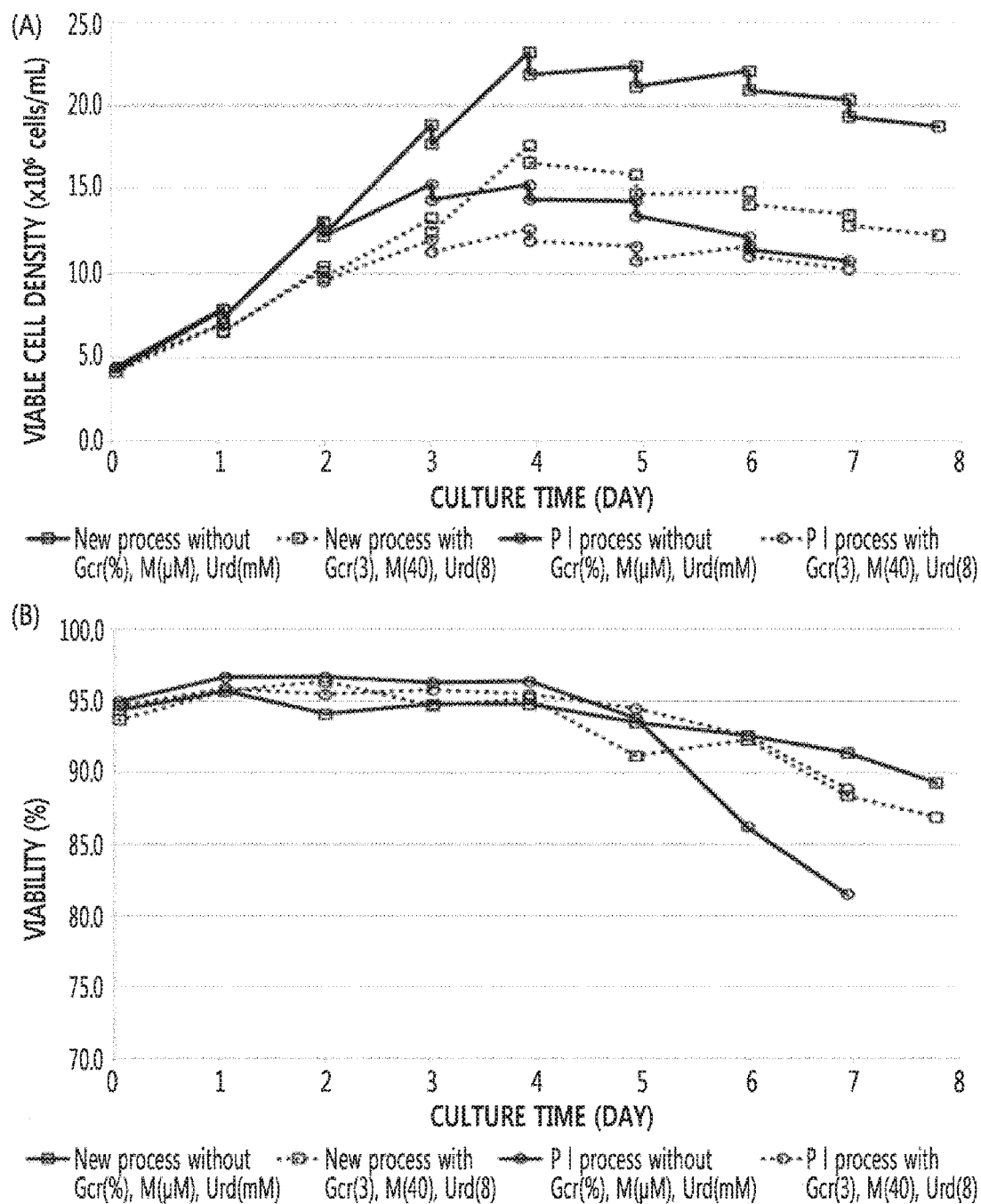

[FIG. 31]
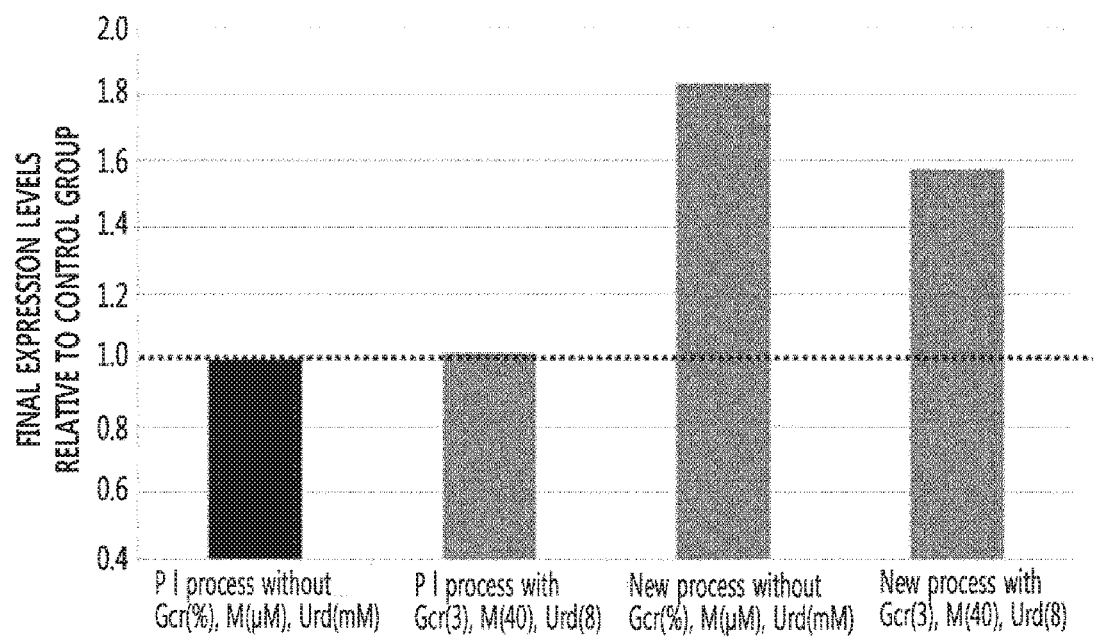

[FIG. 32]
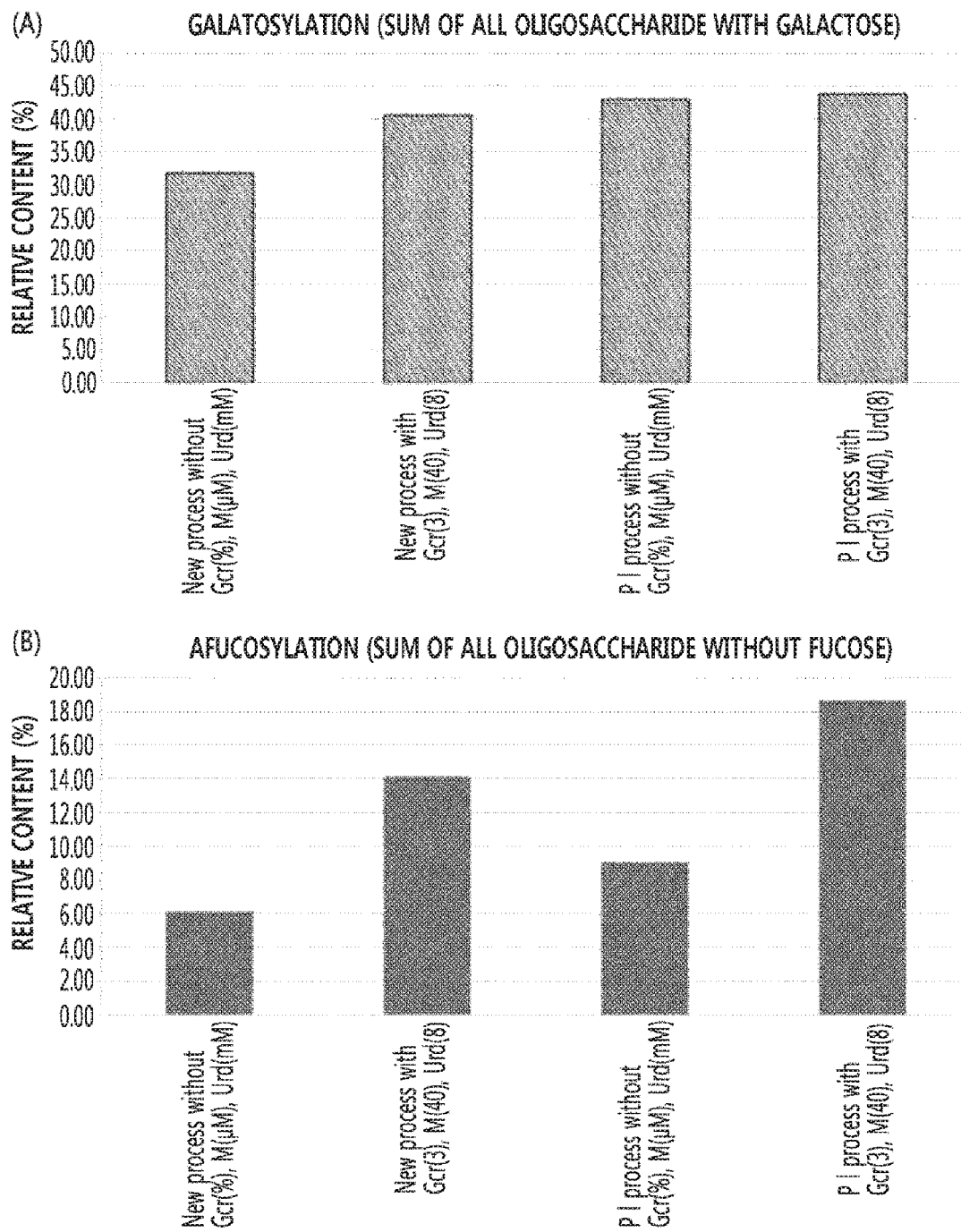

[FIG. 33]
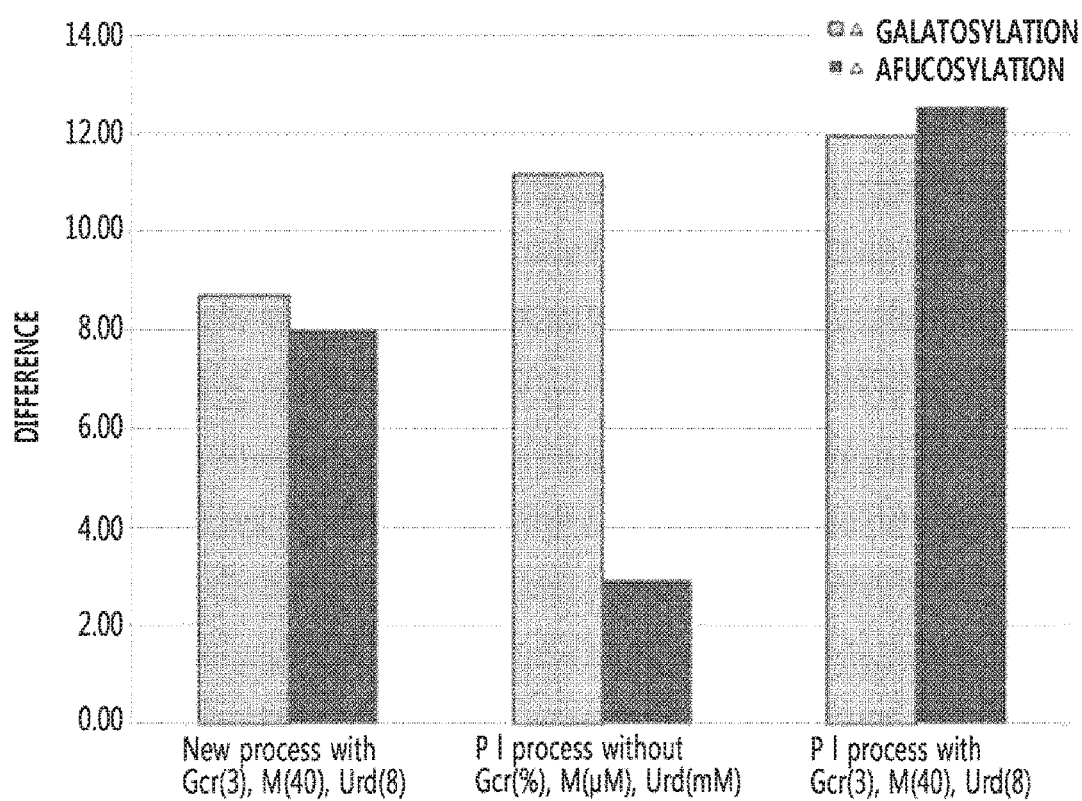

[FIG. 34]
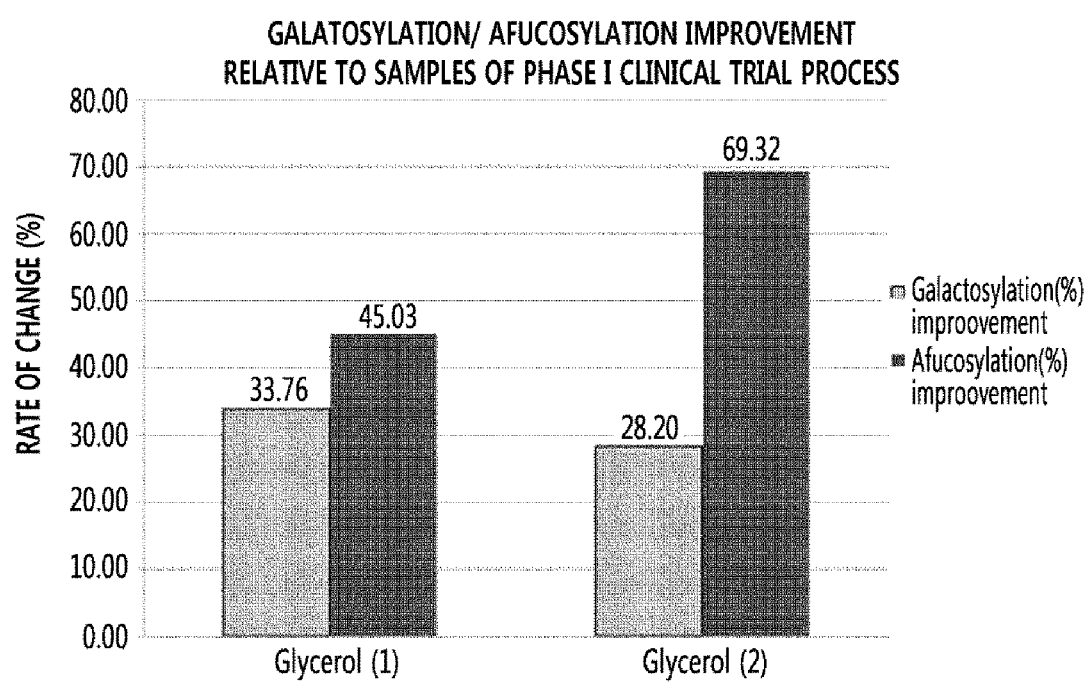

[FIG. 35]
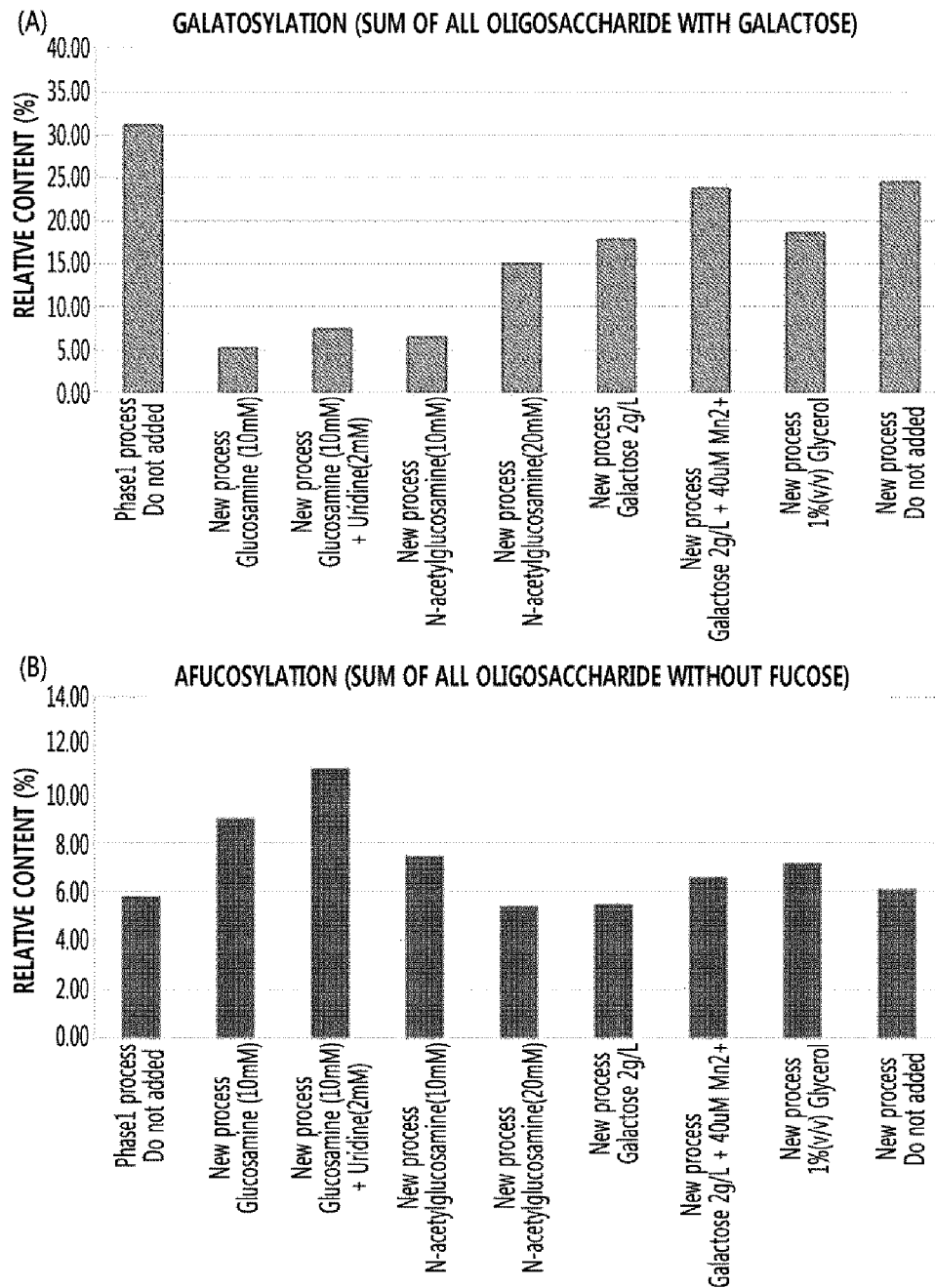

METHOD FOR PREPARING ANTIBODY THROUGH REGULATION OF SUGAR CONTENT OF ANTIBODY

CROSS-REFERENCE TO RELATED APPLICATIONS

This application is a § 371 national stage of PCT International Application No. PCT/KR2015/003310, filed Apr. 2, 2015, claiming priority of Korean Patent Application No. KR 10-2014-0039307, filed Apr. 2, 2014, the content of each of which is hereby incorporated by reference into the application.

BACKGROUND OF THE INVENTION

1. Field of the Invention

The present disclosure relates to a method of preparing an antibody with a regulated sugar chain content, the method including the step of culturing antibody-expressing cells in a medium including glycerol as an additive for regulating the antibody sugar chain content, a method of preparing a high-quality population of antibodies by regulating the sugar content of the antibody to a desired content, and a population of antibodies prepared by the method. Further, the present disclosure relates to a method of regulating the antibody sugar chain content, the method including the step of culturing antibody-expressing cells in a medium including glycerol as an additive for regulating the antibody sugar chain content. Furthermore, the present disclosure relates to a medium composition for regulating the antibody sugar chain content, the medium composition including glycerol as an additive for regulating the antibody sugar chain content.

2. Description of the Related Art

Therapeutic antibodies, e.g., monoclonal antibodies (mAbs) and Fc fusion, proteins, occupy a large share of the current recombinant protein drug market.

Therapeutic effects of the antibody-related drugs are to directly induce apoptosis by inhibiting a signal transduction system of target cells or to induce indirect immune mechanisms such as ADCC (Antibody Dependent Cell-mediated Cytotoxicity) or CDC (Complement Dependent Cytotoxicity), and these two indirect immune mechanisms are called "effector functions" of antibodies. In the fields of biobetters or biosimilars as weld, as new antibodies, effector functions are an important issue, and therefore, studies have been continued for optimization of the functions or securing of in-vitro similarity of effector functions.

Galactosylation of Fc region affects CDC of antibodies. In the galactosylation mechanism, galactose is a building block of the glycosylation chain reaction and binds next to N-acetylglucosamine sugar by galactosyitransferase, and uridine is converted to UTP (uridine triphosphate) by uridine kinase, and then UTP binds to galactose-1-phosphate (galactose-1-P) to produce a galactosylation building block, UDP-galactose. Manganese ($Mn^{2+}$) is a cofactor of galactosyltransferase and functions to improve enzymatic performance.

Studies to improve ADCC of antibodies may be largely divided into engineering of the Fc region itself and sugar chain modification of the Fc region of antibodies. The present inventors have focused on the latter sugar chain modification of the Fc region and intended to regulate the sugar content. Multinational pharmaceutical companies and advanced biotech companies release the next-generation version of antibodies with improved effector functions and persistence by utilizing sugar chain modification technologies and they continuously make efforts to occupy the market, whereas late movers in the same field are working to adapt to the era of biosimilars and to produce biosimilars which are similar to original products in terms of sugar chains as well as physicochemical properties. The reason is that the components and structures of sugar chains greatly affect therapeutic efficacy, retention time in the human body, pharmacological activity, immune response, etc. Accordingly, companies that intend to develop biosimiliar products actively conduct research into biosimilars which have sugar chains as similar as possible to the original products, and therefore, exhibit equivalent therapeutic efficacy and stability and fewer adverse effects such as immune response.

Previously, many literatures reported that core fucosylation in the sugar chain of the Fc region of a recombinant antibody greatly affects ADCC, and many researchers have studied a method capable of regulating core fucosylation. Representative research results are as follows.

A biosynthetic process of GDP-fucose which is a building block of the fucosylation pathway, and enzymes or building blocks which are directly involved in core fucosylation of antibodies are as shown in FIG. 1 (Sawa et al., "Glycoproteomic probes for fluorescent imaging of fucosylated glycans in vivo", PNAS, 2006, p 12372). Methods of regulating core fucosylation by inhibiting synthesis of the enzymes or building blocks which are directly associated with fucosylation have been studied.

Representative enzyme genes which are known to be associated with core fucosylation are GMD (GDP-mannose 4,6-dehyratase) gene and FUT8 (Alpha-1,6-fucosyltransferase) gene, and a method of regulating core fucosylation by inhibiting expression of the two genes or by preparing a FUT8 knock-out CHO host at a gene level has been suggested ((YAMANE-OHNUKI et al., "Establishment of FUT8 knockout Chinese hamster ovary cells: an ideal host cell line for producing completely defucosylated antibodies with enhanced antibody-dependent cellular cytotoxicity.", BIOTECHNOLOGY AND BIOENGINEERING, 2004, p 614-622).

Another method of inhibiting core fucosylation is a method of adding an inhibitor of glycosidase on the glycosylation pathway (FIG. 2, Mossier et al., "Optimal and consistent protein glycosylation in mammalian cell culture", Glycobiology, 2009, p 939). That is, when glycoproteins move from ER to Golgi in cells, they undergo high mannose trimming by glucosidase and mannosidase. At this time, an alpha-mannosidase I inhibitor such as Kifunensine is added to prepare oligo-mannose type glycoproteins, thereby inhibiting fucosylation. This method is easier than a regulation method performed at a gene level such as cell line establishment, etc., and also advantageous in terms of time and cost.

The other fucosylation control method is a method of regulating osmolality during a culturing process, in which a defucosylation level (deFuc %) is decreased with the increasing osmolality in YB2/0 cell line (Yoshinobu et al., Cytotechnology, 2012, p249~265), and there is also a report that mannose 5 glycoforms are increased in CHO cell line as a result of increasing osmolality and extending culture duration (Efren Pacis et al., BIOTECHNOLOGY AND BIOENGINEERING, 2011, p 1078~1088). The high level of mannose 5 glycoforms indicates the high defucosylation level.

On the other hand, Abbott's patents regarding adalimumab (US 2012/0276631 and WO 2012/149137) disclose regulation of antibody sugar chain by using manganese and galactose, and there are literatures that reported galactosylation regarding uridine. However, there have been difficulties in the preparation of antibodies by regulating the sugar chain to a desired content.

Under the background of demanding a technology of increasing ADCC activity by regulating the sugar chain of antibody, the present inventors have made many efforts to develop a method of maintaining the sugar chain content of antibody in purification products upon preparation of biosimilar antibody drugs. As a result, the present inventors developed an additive to be used during a culturing process, and found out a method of consistently preparing a population of antibodies with secured quality or equivalency by regulating the sugar chain content of the antibody at a desired ratio, thereby completing the present invention.

In detail, the present inventors intended to improve ADCC activity of antibodies by controlling additives and conditions in a culturing process during the preparation of recombinant antibodies to regulate sugar chain content. (galactosylation, afucosylation) of antibodies. As a result, the present inventors found that glycerol increases an afucosylation level, and glycerol also increases the afucosylation level similar to that of a control drug in the case of the development of biosimilars. The present inventors also found that glycerol, manganese, and uridine may be used as additives, and similar effects may be obtained in an old process or a new optimized process where different media are used, and the additives and conditions may be widely applied to a method of preparing antibodies by regulating the sugar chain content of antibodies.

SUMMARY OF THE INVENTION

An object of the present invention is to provide a method of preparing an antibody with a regulated sugar chain content, the method including the step of culturing antibody-expressing cells in a medium including glycerol as an additive for regulating the antibody sugar chain content.

Another object of the present invention is to provide a population of antibodies with the regulated sugar chain content, which is prepared by the method.

Still another object of the present invention is to provide a method of regulating the antibody sugar chain content, the method including the step of culturing antibody-expressing cells in a medium including glycerol as an additive for regulating the antibody sugar chain content.

Still another object of the present invention is to provide a medium composition for regulating the antibody sugar chain content, the medium composition including glycerol as an additive for regulating the antibody sugar chain content.

BRIEF DESCRIPTION OF THE DRAWINGS

FIG. 1 illustrates a biosynthesis of GDP-fucose which is a building block of the fucosylation pathway, and enzymes or building blocks directly involved in the core fucosylation of antibody;

FIG. 2 illustrates the glycosylation pathway;

FIG. 3 shows cell growth curves measured under afucosylation-inducing additive conditions;

FIG. 4 shows cell viabilities measured under afucosylation-inducing additive conditions;

FIG. 5 shows final expression levels measured under a fucosylation-inducing additive conditions;

FIG. 6 is a graph showing relative contents of galactosylated glycoforms of antibodies produced under afucosylation-inducing additive conditions;

FIG. 7 is a graph showing relative contents of afucosylated glycoforms of antibodies produced under afucosylation-inducing additive conditions;

FIG. 8 is a graph showing the results of analyzing increase and decrease in galactosylated and afucosylated antibodies, compared to non-added control;

FIG. 9 shows cell growth curves measured under conditions of single or combination treatment of manganese (M), galactose, and uridine (Urd);

FIG. 10 shows cell viabilities measured under conditions of single or combination treatment of manganese (M), galactose, and uridine (Urd);

FIG. 11 shows final expression levels measured under conditions of single or combination treatment of manganese (M), galactose, and uridine (Urd);

FIG. 12 is a graph showing galactosylation contents under conditions of single or combination treatment of manganese (M), galactose, and uridine (Urd);

FIG. 13 is a graph showing afucosylation contents measured under conditions of single or combination treatment of manganese (M), galactose, and uridine (Urd);

FIG. 14 is a graph showing the results of analyzing increase and decrease in galactosylated and afucosylated antibodies, compared to non-added control;

FIG. 15 is a graph showing the results of measuring (A) cell growth and (B) cell viability according to the concentration of glycerol;

FIG. 16 shows the results of measuring final antibody expression levels according to the concentration of glycerol;

FIG. 17 shows the results of measuring sugar chain contents according to the concentration of glycerol, in which (A) galactosylated and (B) afucosylated sugar chain contents are shown;

FIG. 18 is a graph showing the results of measuring (A) cell growth and (B) cell viability in the flask culture experiments using additive mixtures for co-inducing galactosylation and afucosylation of a new process;

FIG. 19 shows the results of measuring the final antibody expression levels in the flask culture experiments using additive mixtures for co-inducing galactosylation and afucosylation of the new process;

FIG. 20 shows the results of analyzing the sugar chain contents in the flask culture experiments using additive mixtures for co-inducing galactosylation and afucosylation of the new process, in which (A) galactosylated and (B) afucosylated sugar chain contents are shown;

FIG. 21 shows the results of analyzing the sugar chain contents in the flask culture experiments using additive mixtures for co-inducing galactosylation and afucosylation of the new process, in which a galactosylation/afucosylation difference (percent change) measured is shown;

FIG. 22 is a graph, showing the results of measuring (A) cell growth and (B) cell viability in the bioreactor culture experiments according to the concentration of glycerol;

FIG. 23 is a graph showing the results of measuring the final antibody expression levels in the bioreactor culture experiments according to the concentration of glycerol;

FIG. 24 shows the results of analyzing the sugar chain contents in the bioreactor culture experiments according to the concentration of glycerol, in which (A) galactosylated and (B) afucosylated sugar chain contents are shown;

FIG. 25 shows the results of analyzing the sugar chain contents in the bioreactor culture experiments according to the concentration of glycerol, in which a galactosylation/afucosylation difference (percent change) measured is shown;

FIG. 26 shows the final selection of new process additives and a graph showing the results of measuring (A) cell growth and (B) cell viability in bioreactor experiments of 3 batches;

FIG. 27 shows the final selection of new process additives and the results of measuring the final antibody expression levels in bioreactor experiments of 3 batches;

FIG. 28 shows the final selection of new process additives and the results of analyzing the sugar chain contents in bioreactor experiments of 3 batches, in which (A) galactosylated and (B) afucosylated sugar chain contents are shown;

FIG. 29 shows the final selection of new process additives and the results of analyzing the sugar chain contents in bioreactor experiments of 3 batches, in which a galactosylation/afucosylation difference (percent change) measured is shown;

FIG. 30 is a graph showing the results of measuring (A) cell growth and (B) cell viability in the experiments of examining the effects of additive components applied to an old process (phase I clinical trial process);

FIG. 31 is a graph showing the results of measuring the final antibody expression levels in the experiments of examining the effects of additive components applied to the old process (phase I clinical trial process);

FIG. 32 shows the results of analyzing the sugar chain contents in the experiments of examining the effects of additive components applied to the old process (phase I clinical trial process), in which (A) galactosylated and (B) afucosylated sugar chain contents are shown;

FIG. 33 shows the results of analyzing the sugar chain contents in the experiments of examining the effects of additive components applied to the old process (phase I clinical trial process), in which a galactosylation/afucosylation difference (percent change) relative to the control group is shown;

FIG. 34 shows the results of analyzing the sugar chain contents in the experiments of examining the effects of additive components, compared to the old process (phase I clinical trial process), in which a galactosylation/afucosylation increase (percent change) relative to that of the sample of the old process is shown; and FIG. 35 shows the results of analyzing the sugar chain contents in the flask culture experiment for the selection of afucosylation-inducing additives, in which (A) galactosylated and (B) afucosylated sugar chain contents are shown.

DETAILED DESCRIPTION OF THE PREFERRED EMBODIMENTS

In order to achieve the above objects, an aspect of the present invention provides a method of consistently preparing a population of antibodies with secured high quality or equivalency, in which sugar chain content of the antibodies is regulated by adding additives to a medium, thereby preparing a population of antibodies including antibodies with a desired sugar chain content. In particular, the regulation of the antibody sugar chain content may be regulation of galactosylation or afucosylation.

Specifically, the method of the present invention may be a method of regulating galactosylation, afucosylation, or galactosylation/afucosylation content of antibodies by adding one or more additives selected from the group consisting of glycerol, manganese, and uridine to a culture medium during a process of producing antibodies, and in particular, a method of preparing antibodies with regulated sugar chain content, including the step of culturing antibody-expressing cells in a medium including glycerol as an additive for regulating the antibody sugar chain content. In the present invention, the medium may further include one or more selected from the group consisting of manganese and uridine as an additive for regulating the antibody sugar chain content, in addition to glycerol.

As used herein, the term "antibody", a substance produced by stimulation of an antigen in the immune system, refers to a substance that specifically binds with a particular antigen to cause an antigen-antibody reaction in the lymph and blood. The antibody of the present invention may include, but is not limited to, preferably all therapeutic antibodies commonly used in the art, more preferably, trastuzumab or pertuzumab which is an antibody targeting HER-2 (Human Epidermal Growth Factor Receptor 2), and most preferably, trastuzumab. The trastuzumab is, also called Herceptin, a humanized antibody against HER2, developed by Genentech, Inc., (USA), which is known as a therapeutic antibody against HER2/neu mainly expressed in breast cancer cells.

In the present invention, the antibody-expressing cells include natural or transfected cells expressing desired antibodies without limitation. With respect to the objects of the present invention, the antibody-expressing cells may be cells expressing antibodies which are a subject of regulation of the sugar chain content. In an embodiment of the present invention, the antibody-expressing cells may be an HD201 cell line expressing trastuzumab (Accession NO: KCTC 12164BP, Date of Deposit: 2012 Mar. 19, Depositary Institution: the Korean Research Institute of Bioscience and Biotechnology/the Korean Collection for Type Cultures). The cells capable of producing antibodies may be preferably animal cells, for example, Chinese hamster ovary cell line (CHO) or mouse myeloma cell line (NSO).

As used herein, the term "transfection" is a method of altering genetic traits of cells by directly introducing DNA into cultured animal cells, and in general, a method of introducing a target gene via a vehicle such as a plasmid, etc. is used. The transfection may be performed according to a common method in the art, preferably, for example, calcium phosphate coprecipitation, DEAE-dextran treatment, electroporation, redistribution, etc.

As used herein, the term "a population of antibodies" means a group of antibodies including antibodies with different sugar chain contents. With respect to the objects of the present invention, the population of antibodies means a group of antibodies including a desired ratio of galactosylated antibodies, afucosylated antibodies, and galactosylated/afucosylated antibodies. The population of antibodies may include only one type of antibody or all of antibodies that are galactosylated or not and antibodies that are afucosylated or not. With respect to the objects of the present invention, the population of antibodies may preferably refer to a group of antibodies with sugar chain contents regulated by the preparation method of the present invention.

In the present invention, the sugar chain content may be one or more contents selected from the group consisting of a galactosylation content and an afucosylation content.

In the present invention, the galactosylation content means a content of antibodies with galactose-bound sugar chains and the afucosylation content means a content of antibodies with fucosyl-free sugar chains. Galactosylation and afucosylation are widely known as important modifications that greatly affect ADCC and CDC of antibodies.

To develop biosimilars, preparation of a product highly equivalent to a control drug in terms of quality (sugar chain content) is one of the most important development points.

The present inventors continued to study for the improvement of N-glycan (galactosylation and afucosylation) similarity between a recombinant protein expressed and obtained by using a trastuxumab gene and a control drug (the product of Original). It was confirmed that when trastuzumab is prepared, the contents of N-glycans, in particular, the contents of galactosylation and afucosylation are lower than those in the control drug, depending on culture conditions. In particular, since the afucosylation content is a very important index for the activity (ADCC) of antibodies, studies have been conducted on additives used in a culturing process in order to improve the quality as equivalent as that of a control drug by increasing the afucosylation content.

In detail, ADCC (Antibody Dependent Cell-mediated Cytotoxicity) activity of antibodies produced during the development of a new process was measured, and as a result, the activity was as low as 60~80% of that of the control drug. This result led to the present invention. As mentioned above, the afucosylation level which plays an important role in ADCC activity was examined by N-glycan analysis, and as a result, the control drug showed the afucosylation level in the range of 8~10%, and HD201 antibody merely showed the afucosylation level in the range of 5~7%. Accordingly, the present inventors performed experiments in order to improve the galactosylation and afucosylation contents.

Before the present invention, experiments were performed under conditions of adding sugar building blocks in order to induce galactosylation, and as a result, there was no great galactosylation effect, but high afucosylation content was observed in the presence of galactose+manganese ($Mn^{2+}$). Based on this condition, changes in the sugar chain content (quality) were examined by varying other conditions.

In an embodiment of the present invention, experiments were performed under conditions where manganese ($Mn^{2+}$) and galactose were added, together with an afucosylation-inducing additive, and where an afucosylation-inducing additive was added without manganese ($Mn^{2+}$) and galactose. As a result, it was confirmed that addition of the two materials, manganese ($Mn^{2+}$) and galactose, is required in order to obtain a galactosylation level equivalent to that of a control drug, and glycerol influences afucosylation. There are no reports of a technology regarding the afucosylation effect of glycerol, and the present inventors developed the technology for the first time.

To determine a proper concentration of glycerol, experiments were performed in a concentration range of 0~3.0% (v/v), and it was confirmed, that the afucosylation content of antibodies is increased with increasing concentration of glycerol. In particular, while the relative afucosylation content was increased, culture performance relative to that of a non-added condition was examined in the similar range of glycerol concentration. As a result, excellent effect was obtained in the glycerol concentration of 1% to 2%.

Further, in a specific embodiment of the present invention, substitutes for manganese and galactose as additives for improving the galactose content were explored, and uridine was selected as a candidate and used to carry out experiments. Of single additions of the three materials, single addition of manganese showed G0F ratio and G1F ratio similar to those of the control drug, compared, to single addition of galactose or uridine, and therefore, it can be seen that manganese is a major factor of galactosylation in a new process. In contrast, upon single addition of uridine, the galactosylation content was increased with increasing concentration of uridine. However, under a high concentration condition (8 mM), growth inhibition and reduction in expression levels were observed, and therefore, it was considered that addition of a high concentration of uridine at the early stage of culture is inadequate for the new process. In terms of afucosylation, three materials of manganese, galactose, and uridine were compared. As a result, it was confirmed that there was little relationship between manganese and galactose, but the afucosylation content was increased with increasing concentration of uridine.

The results of the experiments performed by adding manganese, galactose and uridine in the new process showed that manganese is the most important factor influencing galactosylation of antibodies, and it was found that when uridine is substituted for galactose, it is possible to design a process improved in terms of galactosylation and afucosylation. Therefore, the present inventors carried out experiments by adding combinations of manganese, uridine and glycerol, in order to improve equivalence to the control drug in terms of a fucosylation as weld, as galactosylation.

In a specific embodiment of the present invention, by using combinations of the additive conditions of the experiments carried out so far, experiments were carried out to control galactosylation and fucosylation patterns of the antibody (Trastuzumab) so that they are the most similar to those of a control drug (Herceptin®). As additives for regulating the antibody sugar chain content, manganese which is a main additive for improving galactosylation, glycerol which is an afucosylation-inducing additive, and uridine which may be substituted for galactose and is a co-additive for galactosylation and afucosylation may be used to design experiments.

It was observed that addition of a high concentration of uridine facilitates afucosylation but reduces expression levels by growth inhibition. For this reason, uridine was separately added on day 5 of culture to minimize growth inhibition and high mannose form.

It was confirmed that manganese had the highest effect of facilitating galactosylation, and showed similar effects in a concentration range of 20~120 μM. Further, glycerol showed the effect of facilitating afucosylation proportional to its concentration in the range of 1% to 3%.

These three factors were mixed and added as additives, and as a result, it was confirmed, that uridine had an effect of improving galactosylation, and therefore, uridine was considered to be a substitute for galactose, and also showed an effect of improving afucosylation even the effect is low. Meanwhile, in the flask culture experiments, conditions which are the most similar to those of the control drug (Herceptin® H0717) were found to be addition of uridine (on day 5 of culture) based on the combination of 40 μM manganese+1% glycerol.

In contrast, the result of the bioreactor culture experiments showed that addition of 2% glycerol, rather than 1% glycerol, to a production medium showed high equivalence to the control drug (Herceptin®) in terms of afucosylation. When the afucosylation ratio of the control drug is regarded as 'y', the sample of the old process showed the afucosylation ratio of 0.43, and 2% glycerol-added condition showed the afucosylation ratio of 0.86 which was slightly lower than that of the control drug, but 2 times higher than that of the sample of the old process.

In the results of bioreactor experiments of the additives for improving sugar chain regulation (galactosylation and afucosylation), addition of 2% glycerol showed the effect of increasing the afucosylation ratio, compared to that of the sample of the old process, in the N-glycan profiles, and in terms of galactosylation, addition of manganese and uridine showed the effect of improving galactosylation. However, they do not show complete equivalence to that of the control drug (Herceptin®), and therefore, it was tried to change the concentrations of glycerol and uridine and the addition method.

First, it was intended that feeding was performed by adding 2% glycerol to a feed medium in order to improve the addition effect of glycerol. Uridine was added as a substitute for galactose by increasing its concentration from 4 mM to 8 mM in order to improve the galactosylation effect. Further, in flask experiments performed by adding uridine, pH was measured on the final day of culture. As a result, pH was 6.9. Thus, the culture pH was adjusted from pH 6.8 to pH 6.9 after addition of uridine. In order to maintain pH 6.8 in a bioreactor, $CG_2$ should be fed, but $pCO_2$ tend to continuously increase from day 4 of culture and rapidly increase to 100 mmHg or higher on day 5 of culture. Therefore, referring to the literature reporting that high $pCO_2$ negatively affects glycosylation (Kimura R, 1997), $pCO_2$ was decreased when pH of the main culture was increased to pH 6.9 on day 5 of culture. Reflecting this fact, experiments were designed as follows: All 3 batches were performed by adding additives for regulating the sugar chain content (quality improvement), 40 µM manganese (M) and 2% (v/v) glycerol (Gcr), to production media as for the selection of additives of a new process, and on day 5 of the main culture, 8 mM uridine (Urd) was added, followed by culturing. Consequently, a new process involving addition of 8 mM uridine on day 5 of the culture following addition of 40 µM manganese and 2% glycerol was designed. Further, the glycosylation contents of antibodies which were produced by bioreactor culture of 3 batches under the same conditions were examined, and N-glycan profiles of samples which were obtained from respective batches on day 8 of the main culture were compared with those of the old process. As a result, galactosylation (Sum of all oligosaccharide with galactose) % of HD201P-1102 ref. (In-house standard) was 33.9%, and galactosylation % of 3 batches of the new process was in the range of 41.8~42.2%, which is about 8% higher than that of HD201P-1102. Further, afucosylation (Sum of all oligosaccharide without fucose) % of HD201P-1102 was 3.8%, and afucosylation % of 3 batches of the new process was in the range of 9.1~9.5%, which is about 6% higher than that of HD201P-1102, Compared with the control drug (Herceptin®), galactosylation % of the control drug (Herceptin® Lot.H0717) was 43%, and thus difference in the galactosylation % between the control drug and 3 batches of the new process was less than 2%, and afucosylation % was 8.9%, and thus difference in the afucosylation % between the control drug and the new process was less than 2%, indicating that the conditions are effective in terms of equivalence to the control drug. Oligo-mannose type (Sum of all oligosaccharide with mannose) of the control drug was 1.7%, and oligo-mannose type (4%) of the new process was 2% higher than that of the control drug.

Additionally, the additives (manganese, glycerol, and uridine) for regulating the sugar chain content (Fc N-glycan quality improvement) designed in the new process were applied to the old process (different medium environments) in a small-scale bioreactor to examine whether glycosylation profiles (galactosylation/afucosylation) are regulated. 2% glycerol was added to both of the production culture medium and the feed medium in the new process, but in this experiment, the glycerol concentration was increased to 3%. In the samples collected from the main culture in the bioreactor, N-glycan profiles were compared between the additive-added condition and non-added condition in the old process. The additive-added condition showed galactosylation % of 43.3% and the non-added condition showed galactosylation % of 43%, that is, the additive-added condition showed 1% increase in galactosylation %. Further, the additive-added condition showed afucosylation % of 18.7% and the non-added condition showed afucosylation % of 9.1%, that is, the additive-added condition showed 2-fold increase in the afucosylation %. Furthermore, in the new process, the additive-added condition and the non-added condition were compared. As a result, the additive-added condition showed galactosylation % of 40.5% and the non-added condition showed galactosylation % of 31.8%, that is, the additive-added condition showed 8% increase in the galactosylation %. The additive-added condition showed afucosylation % of 14.1% and the non-added condition showed afucosylation % of 6.1%, that is, the additive-added condition showed 2-fold increase in the afucosylation %, similar to the results in the old process.

It was confirmed that addition of the additives (manganese, glycerol, and uridine) for regulating the sugar chain content (Fc N-glycan quality improvement) developed in the present invention showed similar effects in the old process as well as in the new process.

Analysis of ADCC activity of KD201 antibody was performed according to antibody-dependent cytotoxicity assay's SOP [HD201 antibody-dependent cytotoxicity assay].

Further, in a specific embodiment of the present invention, ADCC activity of antibodies prepared by adding the additives (manganese, glycerol, and uridine) for regulating the sugar chain content of the present invention was measured by a relative ADCC assay which is an in-vitro assay. As a reference material (control drug) of ADCC activity, a currently available original product (Kerceptin®) was used. The experimental, results were expressed, as relative ADCC % (A) determined by $EC_{50}$ values commonly used, and relative ADCC activity % (B) using a relative activity ratio calculated by using PLA s/w. It can be seen that there is a slight difference between the results obtained from $EC_{50}$ and PLA, but entire patterns were the same.

In the small-scale old process, the additive-added condition showed 217.5% of ADCC activity, compared to the control drug, and the non-added condition showed 78.7% of ADCC activity, which is lower activity than that of the control drug. Therefore, when the additives (manganese, glycerol, and uridine) for regulating the sugar chain content (Fc N-glycan quality improvement) were added to the old process, the afucosylation ratio may be increased to 2-fold, leading to 100% or higher improvement in ADCC activity, compared to the non-added condition. In the new process, the additive-added condition showed 130% of ADCC activity, compared to the control drug, and the non-added condition showed 42.7% of ADCC activity, which is the lowest activity, compared to that of the control drug. Therefore, as in the old process using different media, when the additives (manganese, glycerol, and uridine) for regulating the sugar chain content (Fc N-glycan quality improvement) were added to the new process, the afucosylation ratio may be increased to 2-fold, leading to 80% or higher improvement in ADCC activity, compared to the non-added condition.

As confirmed in Examples of the present invention, when a production process of trastuzumab is performed using the additives for regulating the sugar chain content of the present invention, regulation of sugar chain content of antibodies is possible. In particular, there have been no studies or literatures regarding the afucosylation effect of glycerol in Korea or abroad. On the basis of the above experimental results, the present inventors developed a method of preparing antibodies by regulating the sugar chain content using glycerol for the first time.

In the present invention, culturing may be carried out by a method widely known to those skilled in the art under appropriate temperature, medium, and gas conditions depending on antibody-expressing cells. There is no limitation in a method applicable to the antibody preparation of the present invention, such as batch culture, fed-batch culture, continuous culture, a combination thereof, etc.

The preparation method of the present invention may include the steps of (a) culturing antibody-expressing cells in a medium including glycerol and manganese; and (b) culturing the cells cultured in step (a) in a medium further including uridine. In particular, the method may further include the step (c) of culturing the cells cultured in step (b) by adding a feed medium, including glycerol and manganese. The step (a) may be carried out for 3 days to 8 days, and in Examples of the present invention, uridine treatment was carried out on day 5 of culture.

Further, the preparation method of the present invention may include the steps of (a) culturing antibody-expressing cells in a medium including glycerol and manganese; (b) culturing the cells cultured in step (a) in a medium including uridine; and (c) performing fed-batch culture using a medium including glycerol and manganese.

Meanwhile, step (a) and step (b) may be performed by batch culture, and step (c) may be performed by fed batch culture, but are not limited thereto.

Further, the preparation method of the present invention may further include the step of purifying antibodies from a cell culture broth, and the method of purifying the antibodies may be performed by a variety of methods widely known in the art, for example, protein A/G column, HPLC, etc.

The medium of the present invention may include glycerol within a concentration range from 0 to 10%, or from 0.1 to 5% (v/v), and in particular, within a concentration range from 0.5 to 3% (v/v). Further, the medium may include manganese within a concentration range from 0 to 250 µM, or from 10 to 200 µM, and in particular, within a concentration range from 20 to 120 µM. Furthermore, the medium may include uridine within a concentration range from 0 to 20 mM, or from 1 to 10 mM, and in particular, within a concentration range from 4 to 8 mM.

Specifically, the medium of the present invention may include glycerol within a concentration range from 0.5 to 3% (v/v), manganese within a concentration range from 20 to 120 µM, and uridine within a concentration range from 3 to 10 mM.

The type of the manganese of the present invention is not particularly limited, as long as it is non-toxic to the human body, and exemplified by manganese chloride.

With regard to the additives for regulating the sugar chain content included in the medium of the present invention, a ratio of glycerol (%, v/v): manganese (µM) may be 0.5:20, 1:20, 2:20, 3:20, 0.5:40, 1:40, 2:40, 3:40, 0.5:80, 1:80, 2:80, 3:80, 0.5:120, 1:120, 2:120 or 3:120, based on the final concentration of the medium. Further, in the present invention, uridine which is included in the medium of the present invention and constitutes the additives for the regulating the sugar chain content may be added at a concentration of 2 to 8 mM, based on the final concentration of the medium.

In a specific embodiment of the present invention, it was confirmed that when the additives for the regulating the sugar chain content of the present invention may have a ratio of glycerol (%, v/v):manganese (µM):uridine (mM) of 1.0:40:80 or 2.0:40:80, based on the final concentration of the medium, the sugar chain content similar to that of the known control drug, Herceptin® may be obtained.

In the sugar chain content of the antibodies prepared by the preparation method of the present invention, the galactosylation content may be within the range from 35 to 50% and the afucosylation content may be within the range from 8 to 20%.

Another aspect of the present invention provides a population of antibodies with regulated sugar chain content, prepared by the method of the present invention.

The method, population of antibodies, and population of antibodies with regulated sugar chain content are the same as described above.

Still another aspect of the present invention provides a method of regulating the antibody sugar chain content, the method including the step of culturing antibody-expressing cells in a medium including glycerol as an additive for regulating the antibody sugar chain content. The medium may further include one or more selected from the group consisting of manganese and uridine as an additive for regulating the sugar chain content.

The sugar chain content, antibody, antibody-expressing cells, and culture are the same as described above.

Still another aspect of the present invention provides a medium composition for regulating the antibody sugar chain content, the medium composition including glycerol as an additive for regulating the antibody sugar chain content.

The sugar chain content and antibody are the same as described above.

The medium composition for regulating the antibody sugar chain content of the present invention may further include one or more selected from the group consisting of manganese and uridine as additives for regulating the antibody sugar chain content.

As used herein, the term "medium" broadly refers to a nutrient-containing solution which provides nutrients for proliferating cells, and this solution may include essential and non-essential amino acids, vitamins, carbon sources, lipids, trace elements, etc. which are generally required for cell proliferation and/or survival, but is not limited thereto. The medium is preferably formulated at a pH and a salt concentration optimal for cell survival and proliferation, depending on the type of cells to be cultured. The medium may further include a substance widely used in the art as a component enhancing proliferation and/or survival, including hormones and growth factors.

Further, components, excluding the additives for regulating the antibody sugar chain content, in the medium of the present invention may include any components for the production of antibodies widely used in the art, and the components may be easily constituted in accordance with the common sense or experiments of those skilled in the art.

In a specific embodiment of the present invention, the main culture was performed by controlling the additives based on Media A, and the fed batch culture was performed by controlling the additives based on Feed C.

Hereinafter, the present invention will be described in more detail with reference to Examples. However, these Examples are for illustrative purposes only, and the scope of the present invention is not intended to be limited by these Examples.

EXAMPLE 1

Experiment of Additives for Regulating Antibody Sugar Chain 1-1. Flask Culture Experiment for Selection of Afucosylation-Inducing Additives In order to induce galactosylation, experiments were carried out under conditions where sugar building blocks (glucosamine, N-acetylglucosamine, N-acetylmannosamine, galactose, uridine, Manganese ($Mn^{2+}$), glycerol) were added. As shown in the analysis results of the experimental data of FIG. 35, a great galactosylation effect was not observed, but a high afucosylation content was observed. On the basis of these results, in the subsequent studies, galactose+manganese ($Mn^{2+}$) known to show galactosylation-related effects were used in combination, and changes were examined. Further, in order to find out a factor showing the effect when used alone, parallel experiments were carried out under conditions where galactose+manganese ($Mn^{2+}$) were excluded.

In detail, experiments were performed under conditions where manganese ($Mn^{2+}$) and galactose were added, together with the afucosylation-inducing additive, and under conditions where the afucosylation-inducing additive was added without manganese ($Mn^{2+}$) and galactose.

200 g/L stock of galactose was prepared and used, and 40 mM stock of manganese chloride•4 water ($Mn^{2+}$) was prepared and used. Manganese and galactose added to a production medium were diluted, based on 35 mL which is a volume of a main flask culture, and a feed medium was separately divided into 20 mL per conditions, and stocks were diluted, based on a volume of 20 mL, and added.

Each 1 M stock of the afucosylation-inducing additives, glucosamine and N-acetylglucosamine was prepared, and pure glycerol was regarded as 100% and added in a volume ratio (v/v, %), 50 mM stock of sodium butyrate and 50 g/L stock of lactose were prepared and diluted 1/100. Kifunensine, an alpha-mannosidase I inhibitor, is a substance known to have the afucosylation effect, and prepared at a concentration of 100 μg/mL (Qun Zhou et al., 2008; US 2007/0092521 A1).

The experimental conditions are summarized in the following Table 1.

TABLE 1

Conditions for flask culture experiment of afucosylation-inducing additives

| Experimental group | Medium | 2.0 g/L of Galactose + 40 μM $Mn^{2+}$ | Sugar building block |
|---|---|---|---|
| M(40), Gal(2.0) | Media A | added | Not added; Negative control |
| M(40), Gal(2.0), Glucosamine (10) | Media A | added | Glucosamine(10 mM) |
| M(40), Gal(2.0), N-acetylglucosamine(10) | Media A | added | N-acetylglucosamine(10 mM) |
| M(40), Gal(2.0), Glycerol (1) | Media A | added | 1% (v/v) Glycerol |
| M(40), Gal(2.0), Sodium butyrate(0.5) | Media A | added | Sodium butyrate(0.5 mM) |
| M(40), Gal(2.0), Lactose (0.5) | Media A | added | Lactose(0.5 g/L) |
| M(40), Gal(2.0), Kifunensine(10) | Media A | added | Kifunensine(10 ng/mL); Positive control |
| Control | Media A | n/a | Not added; Negative control |
| Glucosamine(10) | Media A | n/a | Glucosamine(10 mM) |
| N-acetylglucosamine(10) | Media A | n/a | N-acetylglucosamine(10 mM) |
| Glycerol(1) | Media A | n/a | 1% (v/v) Glycerol |
| Sodium butyrate(0.5) | Media A | n/a | Sodium butyrate(0.5 mM) |
| Lactose(0.5) | Media A | n/a | Lactose(0.5 g/L) |
| Kifunensine(10) | Media A | n/a | Kifunensine(10 ng/mL); Positive control |

1-2. Cell Culture Results of Flask Culture Experiment of Afucosylation-Inducing Additives In the flask culture for the selection of afucosylation-inducing additives, cell growth profile, cell viability profile, and final expression level profile (titer profile) were measured.

As shown in FIG. 3, the results of cell growth profiles showed that the highest cell growth was observed when manganese and galactose were not added (Control), and growth inhibition was observed when 0.5 mM sodium butyrate was added.

As shown in FIG. 4, the results of cell viability profiles also showed that cell viability was decreased to 80% or less at the end point of the culture when sodium butyrate was added, and cell viability was decreased to 77% at the end point of the culture when 1.0 ng/mL of Kifunensine was added together with manganese and galactose. Other additive conditions showed similar cell growth and cell viability profiles.

Meanwhile, final expression levels relative to that of a control group (titer profile) were measured under afucosylation-inducing additive conditions, and as a result, when glucosamine, N-acetylglucosamine, or glycerol was added, the expression level showed 1.1-fold increase, compared to the control group. In contrast, when sodium butyrate was added, the expression level showed 0.8-fold increase, which was lower than those of other conditions. It seems that such decrease in the expression level is attributed to a reduction in cell growth and cell viability.

1-3. Analysis of Sugar Chain Content of Antibody

To analyze the sugar chain content of antibodies, antibody N-glycan assay was performed. In detail, N-glycan assay was performed according to HD201 N-glycan assay's SOP [N-glycan NP-UPLC assay of HD201], in which antibodies were treated with PNGase to separate only N-glycan structures. Galactosylated and afucosylated glycoforms were analyzed, and each of the calculated relative contents was shown in a graph (FIGS. 6 and 7). Additionally, the results of analyzing increase and decrease in galactosylation and afucosylation, compared to non-added control, were also shown in a graph (FIG. 8).

As shown in FIGS. 6 to 8, the greatest difference between manganese and galactose-added (condition and non-added condition is a difference in the galactosylation content, and high relative galactosylation contents were observed, when the two materials were added, compared to non-added control. In contrast, similar or lower relative galactosylation contents were observed when both of the materials were not added, compared to the control group. These results indicate that both of manganese and galactose are required in order to increase the galactosylation content.

1-4. Experiment of Changes in Antibody Sugar Chain According to Single or Combination Treatment of Manganese (M), Galactose, and Uridine (Urd)

As a method of regulating antibody sugar chain content, a method of using manganese and galactose was previously disclosed (e.g., Abbott, US 2 012/0276631; WO 2012/149197). This experiment was intended to find out other substitutes for manganese and galactose.

The old process is a process for the production of samples for phase I clinical trial at the early stage of development, and the new process is a process developed for phase III clinical trial through process improvement. The new process and the old process are different in the production medium and feed medium, and it was intended that the additives of the present invention were used to increase activity of antibodies by preparing a sugar chain pattern, in particular, afucosylation content similar to that of the original product during a process of developing the new process.

200 g/L stock of galactose was prepared and used, and 40 mM stock of manganese chloride•4 water ($Mn^{2+}$) was prepared and used. Manganese and galactose added to a production medium were diluted, based on 35 mL which is a volume of a main flask culture, and a feed medium was separately divided into 20 mL per conditions, and stocks were diluted, based on a volume of 20 mL, and added.

The experimental conditions are as in the following Table 2.

TABLE 2

Manganese ($Mn^{2+}$), galactose (Gal), and uridine (Urd)-added conditions

| Experimental group | Production medium | Feed medium |
|---|---|---|
| Control(not added) | Media A | Feed C |
| M(40), Gal(2) | Media A + 2 g/L of Gal + 40 μM $Mn^{2+}$ | Feed C + 2 g/L of Gal + 40 μM $Mn^{2+}$ |
| Gal(2), Urd(2) | Media A + 2 g/L of Gal + 2 mM Uridine | Feed C + 2 g/L of Gal + 2 mM Uridine |
| Gal(2) | Media A + 2 g/L of Gal | Feed C + 2 g/L of Gal |
| Gal(4) | Media A + 4 g/L of Gal | Feed C + 4 g/L of Gal |
| Gal(8) | Media A + 8 g/L of Gal | Feed C + 8 g/L of Gal |
| M(40) | Media A + 40 μM $Mn^{2+}$ | Feed C + 40 μM $Mn^{2+}$ |
| M(80) | Media A + 80 μM $Mn^{2+}$ | Feed C + 80 μM $Mn^{2+}$ |
| M(120) | Media A + 120 μM $Mn^{2+}$ | Feed C + 120 μM $Mn^{2+}$ |
| Urd(2) | Media A + 2 mM Uridine | Feed C + 2 mM Uridine |
| Urd(4) | Media A + 4 mM Uridine | Feed C + 4 mM Uridine |
| Urd(8) | Media A + 8 mM Uridine | Feed C + 8 mM Uridine |

As shown in FIG. 9, the results of flask culture showed that most cell growth profiles were similar when manganese and galactose were added, and the highest peak cell density was observed when the additive was not added (control) and only 40 μM of manganese was added. When uridine (Urd) was added at a concentration of 8 mM, growth inhibition was observed at the early stage of culture, and when uridine was added at a concentration of 4 mM, the reduction in the cell density was greatly increased at the late stage of culture.

In cell viability profiles (FIG. 10), viability was rapidly reduced when 8 mM of uridine was added, and other conditions showed similar patterns.

As shown in the antibody expression level profiles (titer profiles) of FIG. 11, manganese-added conditions showed about 0.9~1.1 of the relative content ratio, compared to the non-added condition (control) and galactose-added conditions showed 0.9~1.0 of the relative content ratio. When uridine was added, a reduction in the expression level relative to that of the non-added condition (Control) was increased with increasing concentration of uridine. When 8 mM of uridine was added, the relative content ratio was decreased to 0.36, compared to that of the non-added condition (Control), suggesting that this reduction is attributed to a reduction in the expression levels due to cell growth inhibition. Therefore, it was confirmed that when manganese is added within the concentration range of 40 μM~120 μM, there is no influence on the process.

1-5. Analysis of Sugar Chain Content of Antibody

As in the conditions of Table 2, manganese, galactose, and uridine were added to flasks at different concentrations, sugar chain contents (glycosylation quality) of culture products were examined. In detail, galactosylated and afucosylated glycoforms were analyzed, and each of the calculated relative contents was shown in a graph (FIGS. 12 and 13). Additionally, the results of analyzing increase and decrease in galactosylation and afucosylation, compared to non-added control, were also shown in a graph (FIG. 14).

As shown in FIG. 12, the results of calculating the galactosylation content showed that when 40 μM of manganese and 2 g/L of galactose were added at the same time, the highest content was observed, compared to the control (non-added condition), and of the single additions of the three materials, manganese-added experimental groups showed higher values than galactose- or uridine-added experimental groups, indicating that manganese is a major factor of galactosylation in the new process. In contrast, upon single addition of uridine, the galactosylation content was increased with increasing concentration of uridine. However, under a high concentration condition (8 mM), growth inhibition and reduction in expression levels were observed, and therefore, it was considered that addition of a high concentration of uridine at the early stage of culture is inadequate for the new process.

As shown in the results of calculating the afucosylation content of FIG. 13, three materials of manganese, galactose, and uridine were compared. As a result, it was confirmed that manganese and galactose showed no effects, but the afucosylation (content was increased, with increasing concentration of uridine. In a graph (FIG. 14) showing a difference in galactosylation/afucosylation, compared to non-added group, it was confirmed that when manganese was added, galactosylation was enhanced to 10% or more, compared to non-added group, and the afucosylation was enhanced with increasing concentration of uridine, compared to non-added group.

According to these results of examining addition effects of manganese, galactose, and uridine in the new process, it was confirmed that manganese is the most important factor in the galactosylation of antibodies, and when uridine is substituted for galactose, improvement in terms of galactosylation and afucosylation may be achieved.

In the subsequent experiments, manganese, uridine and glycerol were added in combination, in order to improve galactosylation/afucosylation equivalence to a commercial control drug (Herceptin®) in terms of developing biosimilars.

1-6. Flask Culture Experiment of Changes in Sugar Chain According to Glycerol Addition In this experiment, glycerol (Gcr) obtained through selection of afucosylation-inducing additives, in addition to manganese and galactose, was added by varying its concentration, and the effects were examined.

Glycerol is a substance well known as an anti-freezing agent and a protein stabilizer, and there is a literature reporting that glycerol increases the expression levels of recombinant proteins or the content of sialic acid (Rodriguez et al, 2005, Chi-Hsien Liu 2007), but there is no mention about afucosylation of antibodies related to the present invention.

Therefore, in order to examine the effect of glycerol on afucosylation of antibodies, experiments were carried out. In detail, glycerol was added at a concentration of 0, 0.5, 1 or 2% (v/v) and the afucosylation content according to the glycerol addition was measured.

The experimental conditions are as in the following Table 3.

TABLE 3

Conditions for flask culture experiment of afucosylation-inducing additive, glycerol

| Experimental group | Production medium (A) | Feed medium (C) |
|---|---|---|
| M(40), Gal(2), Gcr(0) | Media A + 2 g/L of Galactose + 40 μM $Mn^{2+}$ | Feed C + 2 g/L of Galactose + 40 μM $Mn^{2+}$ |
| M(40), Gal(2), Gcr(0.5) | Media A + 2 g/L of Galactose + 40 μM $Mn^{2+}$ + 0.5% glycerol | Feed C + 2 g/L of Galactose + 40 μM $Mn^{2+}$ |
| M(40), Gal(2), Gcr(1.0) | Media A + 2 g/L of Galactose + 40 μM $Mn^{2+}$ + 1% glycerol | Feed C + 2 g/L of Galactose + 40 μM $Mn^{2+}$ |
| M(40), Gal(2), Gcr(2.0) | Media A + 2 g/L of Galactose + 40 μM $Mn^{2+}$ + 2% glycerol | Feed C + 2 g/L of Galactose + 40 μM $Mn^{2+}$ |

Cell growth profiles and cell viability profiles according to the concentrations of glycerol were measured. As shown in the results of FIG. 15, similar cell growth and cell viability were observed under glycerol-added condition and non-added condition. It was confirmed that cell viability was slightly low, compared to non-added condition, on the final day of culture.

Further, as shown in the results of measuring final antibody expression levels of FIG. 16, the antibody expression levels were increased with increasing concentration of glycerol, compared to non-added condition. When 2.0% of glycerol was added, the expression level was increased 1.1-fold or higher, which was recorded as the highest relative content ratio.

1-7. Analysis of Sugar Chain Content of Antibody

Contents of galactosylated and afucosylated sugar chains were measured according to the glycerol concentration, under the conditions of Table 3.

As shown in FIG. 17, as the glycerol concentration was increased, galactosylation was slightly decreased, but the galactosylated antibody contents were maintained at 40% or more, showing no great effects (FIG. 17 (A)), and in terms of afucosylation, as the glycerol concentration was increased, the afucosylated antibody contents were remarkably increased, compared to the control (non-added group) (FIG. 17(B)).

1-8. Flask Culture Experiment of Additive Mixture for Co-Induction of Galactosylation and Afucosylation in New Process By using combinations of the experimental results of the additive conditions obtained in the above Examples, experiments were carried out to examine a condition under which a population of finally prepared antibodies shows the most similar sugar chain contents, namely, galactosylation and afucosylation contents to those of the control drug (Herceptin®).

In the present experiment, manganese (M) which is a main factor for the improvement of galactosylation, glycerol (Gcr) which is an afucosylation-inducing additive, and uridine (Urd) as a substitute for galactose, which is a cofactor of galactosylation and afucosylation, were used as additives.

Meanwhile, the previous experiment (Examples 1-4) showed that addition of uridine with a concentration of 4 mM or higher facilitates afucosylation but reduces expression levels by growth inhibition. In the present experiment, therefore, 4 mM of uridine was separately added on day 5 of the main culture as in the experimental conditions of the following Table 4 to minimize growth inhibition and high mannose form.

The previous experiment (Examples 1-4) confirmed that manganese (M) had the highest effect of facilitating galactosylation, and showed similar effects in the concentration range of 40 to 120 μM.

In this experiment, 40 μM or less of manganese was added to a production medium and a feed medium.

Lastly, glycerol was added to only the production medium at a concentration of 1% and 2% which showed effects in the above experiment of glycerol addition (Example 1-6).

The experimental conditions are summarized in the following Table 4.

TABLE 4

Flask culture conditions of additive mixtures for induction of galactosylation and afucosylation in new process

| Experimental group | Production medium(A) | | Uridine | Feed medium(C) |
|---|---|---|---|---|
| | Additive | Glycerol (Gcr, v/v %) | | |
| M(40), Galactose(2.0) | 2 g/L of Galactose + 40 μM manganese | n/a | n/a | 2 g/L of Galactose + 40 μM manganese |
| M(40), Gcr(1) | 40 μM manganese | 1% | n/a | 40 μM manganese |
| M(40), Gcr(1), Urd(4) | 40 μM manganese | 1% | 4 mM on day 5 of culture | 40 μM manganese |
| M(40), Gcr(2) | 40 μM manganese | 2% | n/a | 40 μM manganese |
| M(40), Gcr(2), Urd(4) | 40 μM manganese | 2% | 4 mM on day 5 of culture | 40 μM manganese |
| M(20), Gcr(1) | 20 μM manganese | 1% | n/a | 20 μM manganese |
| M(20), Gcr(1), Urd(4) | 20 μM manganese | 1% | 4 mM on day 5 of culture | 20 μM manganese |
| M(20), Gcr(2) | 20 μM manganese | 2% | n/a | 20 μM manganese |
| M(20), Gcr(2), Urd(4) | 20 μM manganese | 2% | 4 mM on day 5 of culture | 20 μM manganese |

As in FIG. 18 showing the results of examining cell growth profiles and cell viability profiles by flask culture under the conditions of Table 4, most cell growth profiles were similar when manganese (M) was added, but addition of 2% glycerol showed a lower cell growth rate than addition of 1% glycerol. Similar peak cell density was observed under non-glycerol added condition (40 μM manganese+2.0 g/L galactose) and 1% glycerol-added condition, suggesting that addition of 1% glycerol do not affect cell growth efficiency in the old process. Since uridine was added on day 5 of the main culture, growth inhibition at the early stage of culture did not occur, but a reduction in cell viability was increased after addition of uridine, compared to non-added condition.

The results of examining the final expression levels (FIG. 19) showed that other conditions than non-glycerol and uridine-added condition (40 µM manganese+2.0 g/L galactose) showed similar or higher expression levels.

1-9. Analysis of Sugar Chain Content of Antibody

Contents of galactosylated and afucosylated sugar chains were measured according to combinations of the additives under the conditions of Table 4. In detail, peak areas of the N-glycan analysis profiles were calculated as galactosylation and afucosylation contents.

As shown in FIG. 20, compared to non-uridine added condition, galactosylation contents were increased under conditions where uridine was added on day 5 of culture, based on a combination of 40 µM manganese+1% glycerol. In terms of afucosylation, compared to non-uridine added conditions, afucosylation contents were increased when 4 mM of uridine was added. Compared to non-uridine added condition, galactosylation contents were increased under conditions where uridine was added on day 5 of culture, based on a combination of 40 µM manganese+2% glycerol. In terms of afucosylation, compared to non-uridine added conditions, afucosylation contents were increased when 4 mM of uridine was added. In particular, afucosylation contents were increased in proportional to the amount of glycerol added.

Compared to non-uridine added condition, galactosylation (contents were increased under conditions where uridine was added on day 5 of culture, based on a combination of 20 µM manganese+1% glycerol. In terms of afucosylation, compared to non-uridine added conditions, afucosylation contents were increased. Similar patterns were observed under conditions where uridine was added, based on a combination of 20 µM manganese+2% glycerol.

Taken together, it was confirmed that addition of uridine to the new process improves galactosylation, and therefore, uridine may be substituted for galactose. It was also confirmed that uridine slightly improves afucosylation.

As a control group, 2.0 g/L of galactose was only added to the new process, and a galactosylation/afucosylation difference (percent change) was examined according to addition of manganese, glycerol, and uridine. As a result, FIG. 21 showed that the galactosylation content was increased to 6~13% by addition of manganese, and the afucosylation content was increased to 1.5~4% by addition of glycerol.

EXAMPLE 2

Experiment of Additives for Regulating Sugar Chain at Bioreactor Level

On the basis of the flask culture experimental results of Example 1, it was examined whether regulation of antibody sugar chain is possible in a bioreactor.

2-1, Bioreactor Experiments by Varying Concentration of Glycerol

To examine afucosylation by addition of glycerol as in the previous flask culture experimental results of Example 1-6, the present experiment was carried out at a reactor level.

As in Example 1-6, the glycerol was added to only the production medium at a concentration of 1% and 2% (v/v) shown in the following Table 5. Glycerol added to the production medium was prepared by diluting pure solution (100%), based on 3.5 L which is a volume of a main reactor culture, and no glycerol was added to a feed medium. It was intended that the additives such as manganese and glycerol were used to achieve galactosylation and afucosylation contents similar to those of the control drug (Herceptin®) during a process of developing the new process.

The experimental conditions at a reactor level are summarized in the following Table 5.

TABLE 5

| Conditons for bioreactor experiments by varying concentration of glycerol | | | |
|---|---|---|---|
| Experimental group | Production medium (A) | | Feed medium (C) |
| | Additive | Glycerol (Gcr, v/v %) | |
| Control | n/a | n/a | n/a |
| glycerol (1) | 2 g/L of Galactose + 40 µM Manganese | 1% | 2 g/L of Galactose + 40 µM Manganese |
| glycerol (2) | 2 g/L of Galactose + 40 µM Manganese | 2% | 2 g/L of Galactose + 40 µM Manganese |

Culturing was carried out in a bioreactor under the conditions of Table 5, and cell growth profiles and cell viability profiles were measured. As in the results of FIG. 22, addition of 1% glycerol showed high cell growth profiles, compared to addition of 2% glycerol (about 10% difference, based on peak cell density), and showed similar high cell growth profiles to those of non-added condition.

The results of the final relative expression levels (FIG. 23) showed that all glycerol-added groups showed high final relative expression levels, compared to non-added group, on the final day of culture.

2-2. Analysis of Sugar Chain Content of Antibody

Contents of galactosylated and afucosylated sugar chains were measured according to combinations of the additives under the conditions of Table 5. In detail, the results of the N-glycan analysis in culture broths cultured for 8 days in a bioreactor of 2 units (addition of 1% or 2% of glycerol) were calculated as galactosylation content (A) and afucosylation content (B).

As shown in FIG. 24, the reactor culture experimental results showed that afucosylation contents were increased by addition of 2% glycerol, rather than addition of 1% glycerol, to the production medium.

As shown in FIG. 25, the results of measuring the galactosylation/afucosylation contents relative to those of the control group (no manganese, galactose and glycerol added) showed that the additives increased galactosylation to 12% or higher, and also increased afucosylation to 1.5%, compared to non-added control group. As shown in FIG. 34, this effect of increasing the afucosylation content was about 2 times higher than that of the previous sample of the phase I clinical trial.

2-3. Final Selection of Additives for New Process and Bioreactor Experiment of 3 Batches As confirmed in Example 2-2, addition of 2% glycerol showed the effect of improving afucosylation on N-glycan profiles, compared to non-added condition, and as confirmed in Example 1, addition of manganese and uridine showed the effect of improving galactosylation. In terms of equivalency to the control drug (Herceptin®), glycerol was added to a production medium and a feed medium, and uridine was added on day 5 of culture at a concentration of 8 mM. 3-batch repeated culture was performed.

In detail, glycerol was added to only the production medium in the previous experiment (Example 2-1), but in order to increase the addition effect, 2% glycerol was also added to the feed medium for feeding. When a high concentration of glycerol is added from the beginning of culture, there is a concern about growth inhibition. Therefore, 2% glycerol was equally added to the feed medium, and a dilution effect by feeding was intended to eliminate.

Of manganese and galactose, galactose was substituted by uridine, and to increase the galactosylation effect, the concentration of uridine was increased from 4 mM to 8 mM. Further, in the flask experiment to which uridine was added, pH on the final day of culture was measured. As a result, pH was about pH 6.9. In this experiment, after addition of uridine, culture pH was increased from pH 6.8 to pH 6.9, because pH may cause the effect difference due to additive concentrations between the flask and the bioreactor.

When pH is intended to maintain at 6.8 in the reactor, pCO tend to continuously increase from day 4 of culture and rapidly increase to 100 mmHg or higher on day 5 of culture. Therefore, it was expected that $pCO_2$ may be decreased when pH of the main culture is increased to pH 6.9 on day 5 of culture, referring to the literature reporting that high $pCO_2$ negatively affects glycosylation (Kimura R, 1997).

The experimental conditions considering this fact are summarized in the following Table 6. With regard to the following conditions, all 3 batches were equally performed by adding additives for regulating the sugar chain content (quality improvement), 40 μM manganese (M) and 2% (v/v) glycerol (Gcr), to production media (media A), and on 5 day of the main culture, 8 mM uridine (Urd) was added, followed by culturing.

TABLE 6

Conditions for final selection of additives for new process and bioreactor experiments of 3 batches

| Experimental group | Production medium | Urd | Feed medium |
| --- | --- | --- | --- |
| New process control | Media A | n/a | Feed C |
| New process batch #1 | Media A + | 8 mM on | Feed C + |
| New process batch #2 | Glycerol 2% | day 5 | Glycerol 2% |
| New process batch #3 | (v/v) + 40 μM manganese | | (v/v) + 40 μM manganese |

As in FIG. 26 showing the results of measuring cell growth profiles and cell viability profiles by performing culture in the bioreactor under the conditions of Table 6, cell growth profiles showed that a peak cell density was about 18 to $24×10^6$ cells/mL, similar to that of the non-added control group.

It was found that the final relative expression level (FIG. 27) was about 1.05 on the final day of the main culture, which was slightly higher than or similar to that of the non-added control group.

2-4 Analysis of Sugar Chain Content of Antibody

The galactosylated and afucosylated sugar chain contents of HD201 antibodies, which were produced by a bioreactor culture of 3 batches by the new process under conditions of adding 3 mM uridine on day 5 of culture on the basis of 40 μM manganese and 2% glycerol of Table 6, were measured. In detail, N-glycan profiles of the samples on day 8 of the main culture were compared between each batch and non-added control group. As a result, galactosylation (Sum of all oligosaccharide with galactose) % of the control group was 31.8% and galactosylation (Sum of all oligosaccharide with galactose) % of 3 batches of the new process was 41.8 to 42.2%, showing about 10% increase. Further, afucosylation (Sum of all oligosaccharide without fucose) % of the non-added control group was 6.1% and afucosylation (Sum of all oligosaccharide without fucose) % of 3 batches of the new process was 9.1~9.5%, showing about 3% increase.

These results were compared to those of the control drug (Herceptin®). As a result, galactosylation % of the control drug (Herceptin® Lot.H0717) was 43%, showing a difference of 2% or less, compared to that of 3 batches of the new process, and afucosylatron % of the control drug was 8.9%, showing a difference of 1% or less, compared to that of the new process, indicating remarkably excellent effects in terms of equivalence to the control drug.

2-5. Effect of Application of Additive Composition to Old Process

It was examined whether desired glycosylation profiles (galactosylation/afucosylation) may be regulated when the additive compositions (manganese, glycerol, and uridine) developed in the new process by the above Examples are applied to the old process in a small-scale bioreactor, and thus it was confirmed whether the additives showed the similar effects in the old process as well as in the new process.

2% glycerol was added to the production medium and the feed medium in the new process, but the concentration of glycerol was increased to 3% in the old process, and then an increase in the afucosylation content according to increase in the concentration of glycerol added was examined. Meanwhile, manganese and uridine were added in the same concentrations as in the new process.

In detail, in phase I clinical trial of small scale, 40 μM manganese (M) and 3% (v/v) glycerol (Gcr) as the additives for regulating sugar chain content (quality improvement additives) were added to a production medium (media D), and manganese and glycerol were also added to a feed medium (Feed A) at the same concentrations as in the production medium. In the new process, 40 μM manganese (M) and 3% (v/v) glycerol (Gcr) as the additives for regulating sugar chain content (Fc N-glycan quality improvement) were added to a production medium (media A), and a feed medium (Feed C), respectively. Experimental groups cultured by equally adding 8 mM uridine (Urd) on day 5 of the main culture in both the old process and the new process were compared to a control group to which the additives for regulating sugar chain content (Fc N-glycan quality improvement) were not added.

The experimental conditions are summarized in the following Table 7.

TABLE 7

Conditions for application of additive to new process and old process

| Experimental group | Production medium | Urd | Feed medium |
| --- | --- | --- | --- |
| New process without Gcr, M, Urd | Media A | n/a | Feed C |
| New process with Gcr(3), M(40), Urd(8) | Media A + Glycerol 3% (v/v) + 40 μM manganese | 8 mM on day 5 | Feed C + Glycerol 3% (v/v) + 40 μM manganese |
| Old process (P I) without Gcr, M, Urd | Media D | n/a | Feed A |
| Old process(P I) with Gcr(3), M(40), Urd(8) | Media D + Glycerol 3% (v/v) + 40 μM manganese | 8 mM on day 5 | Feed A + Glycerol 3% (v/v) + 40 μM manganese |

Bioreactor culture was performed under the conditions of Table 7 to measure cell growth profiles and cell viability profiles. As shown in FIG. 30, a difference in the peak cell density between non-additive added new process and additive-added new process was about 24% on cell growth profiles, and cell growth inhibition by addition of additives was observed. Cell growth inhibition by addition of additives was also observed in the old process. It is construed that the cell growth inhibitions are caused by addition of 3% glycerol among the additives, and the previous experiments showed that cell growth inhibitions tend to increase with increasing (concentration of glycerol.

A difference in cell growth profiles between the new process and the old process was confirmed by comparing a non-additive added old process with a non-additive added new process and comparing an additive-added old process with an additive-added new process. A difference in the peak cell density between non-added conditions was about 34%, indicating that a large cell mass was observed in the new process. Further, a difference in the peak cell density between additive-added conditions was about 28%, and the new process showed higher peak cell density than the old process. In the old process, the main culture was carried out for 7 days, and therefore, in the small-scale batch, culture was also carried out for 7 days.

Cell viability (B) was maintained at 80% or more in the additive-added conditions and non-additive added conditions upon termination of the culture. It was considered that the high reduction rate in the viability after day 5 of culture in the non-additive added old process is attributed to depletion of glucose after day 3 of culture.

The results of the final relative expression levels (FIG. 31) showed that the old process showed similar patterns on day 7 of culture irrespective of the additive addition, whereas the new process showed a 13% lower expression level in the additive-added condition than in the non-additive added condition. The expression level of the new process relative to that of the old process was 1.8, indicating 80% or more increase in productivity.

2-6. Analysis of Sugar Chain Content of Antibody

The galactosylated and afucosylated sugar chain contents of antibodies produced under the conditions of Table 7 were measured. The present experiment was carried out in order to compare the conditions where additives (manganese, glycerol, and uridine) for regulating sugar chain content (quality improvement) were added or not in the new process and the old process.

In detail, the glycosylation contents (glycosylation quality) of the products of bioreactor culture samples were examined by N-glycan analysis, and the resulting galactosylation and afucosylation contents were illustrated. The N-glycan profiles of the samples recovered from the main culture were compared between additive-added condition and non-added condition in the old process. As a result, the galactosylation content (%) was 43.8% in the additive-added condition and 43% in the non-added condition, showing about 1% increase in the additive-added condition. The afucosylation content (%) was 18.7% in the additive-added condition and 9.1% in the non-added condition, showing about 2-fold increase in the additive-added condition.

In the new process, the additive-added condition was compared with the non-added condition. As a result, the galactosylation content (%) was 40.5% in the additive-added condition and 31.8% in the non-added condition, showing about 8% increase in the additive-added condition. The afucosylation content (%) was 14.1% in the additive-added condition and 6.1% in the non-added condition, showing about 2-fold increase in the additive-added condition, like in the old process.

These experimental results showed that the additions of the additives for regulating the antibody sugar chain content consisting of manganese, glycerol, and uridine of the present invention have similar effects in the old process as well as in the new process where different media are used, suggesting that the corresponding additives may be used any process without limitation in the media.

EXAMPLE 3

Examination of ADCC Activity

Analysis of ADCC activity of HD201 antibody was carried out according to antibody-dependent cytotoxicity assay's SOP [HD201 antibody-dependent cytotoxicity assay].

ADCC activity of antibodies prepared by adding the additives (manganese, glycerol, and uridine) for regulating the sugar chain content (Fc N-glycan quality improvement) in small-scale old process and new process was measured by a relative ADCC assay which is an in-vitro assay. As a reference material (control drug) of ADCC activity, a currently available original product (Herceptin®) H4158B03 150 mg) was used.

TABLE 8

Analysis of ADCC activity of HD201 antibody

| RUN | Sample | EC50 (ng/mL) | Relative % | Activity ratio | Relative ratio |
|---|---|---|---|---|---|
| 1 | Herceptin H4158B03 | 22.6 | 100.0 | n/a | 100.0 |
|   | New Process with Fc N-glycan quality improvement additives | 20.6 | 109.7 | 1.3 | 130.0 |
| 2 | Herceptin H4158B03 | 22.9 | 100.0 | n/a | 100.0 |
|   | Phase I Process with Fc N-glycan quality improvement additives | 14.5 | 157.9 | 2.2 | 217.5 |
| 3 | Herceptin H4158B03 | 18.4 | 100.0 | n/a | 100.0 |
|   | Phase I Process with Fc N-glycan quality improvement additives | 25.5 | 72.2 | 0.8 | 78.7 |
| 4 | Herceptin H4158B03 | 19.7 | 100.0 | n/a | 100.0 |
|   | New Process without Fc N-glycan quality improvement additives | 32.7 | 60.2 | 0.4 | 42.7 |

Relative activity ratio (by PLA s/w)

The experimental results were expressed as relative ADCC % (A) determined, by $EC_{50}$ values commonly used, and relative ADCC activity % (B) using a relative activity ratio calculated by using PLA s/w. It can be seen that there is a slight difference between the results obtained from $EC_{50}$ and PLA, but entire patterns were the same.

In the small-scale old process, the additive-added condition showed 217.5% of ADCC activity, compared to the control drug, and the non-added condition snowed 78.7% of ADCC activity, which is lower activity than that of the control drug. Therefore, when the additives (manganese, glycerol, and uridine) for regulating the sugar chain content (Fc N-glycan quality improvement) were added to the old process, the afucosylation ratio may be increased to 2-fold, leading to 100% or higher improvement in ADCC activity, compared to the non-added condition. In the new process, the additive-added condition showed 130% of ADCC activity, compared to the control drug, and the non-added condition showed 42.7% of ADCC activity, which is the lowest activity, compared to that of the control drug. Therefore, as in the old process using different media, when the additives (manganese, glycerol, and uridine) for regulating the sugar chain content (Fc N-glycan quality improvement) were added to the new process, the afucosylation ratio may be increased to 2-fold, leading to 30% or higher improvement in ADCC activity, compared to the non-added condition.

Taken together, the above results showed that improvement of the afucosylation content of antibodies by using glycerol was demonstrated for the first time in the present invention, and a process of regulating sugar chain content of antibodies by using manganese and uridine together with glycerol was developed.

Based on the above description, it will be understood by those skilled in the art that the present invention may be implemented in a different specific form without changing the technical spirit or essential characteristics thereof. Therefore, it should be understood that the above embodiment is not limitative, but illustrative in all aspects. The scope of the invention is defined by the appended claims rather than by the description preceding them, and therefore all changes and modifications that fall within metes and bounds of the claims, or equivalents of such metes and bounds are therefore intended to be embraced by the claims.

Effect of the Invention

A preparation method of antibodies according to the present invention may be used to prepare a desired high-quality population of antibodies by regulating the sugar chain content of the antibody. Further, in terms of the development of biosimilars, the method of the present invention may be used to regulate the sugar chain content of antibodies, thereby preparing antibodies having high equivalence to a control drug. Since the sugar chain content may be regulated by a medium composition, the regulation method is easy and efficient in terms of time and cost, and therefore, widely applied to the fields of antibody preparation.

What is claimed is:

1. A method for preparing a recombinant antibody with a regulated sugar chain content, the method comprising: culturing Chinese hamster ovary (CHO) cells expressing the recombinant antibody in a medium comprising: as additives for regulating the sugar chain content of the antibody, glycerol at a concentration of 0.1 to 5% (v/v) and either (i) manganese at a concentration of 10 to 200 µM or (ii) uridine at a concentration of 1 to 10 mM, or both (i) and (ii); wherein the regulated sugar chain content is a sugar chain content in which afucosylation and galactosylation is increased compared to the sugar chain content of the same antibody produced in a medium not containing said additives.

2. The method of claim 1, wherein the medium comprises as additives glycerol at a concentration of 0.1 to 5% (v/v), and both (i) manganese at a concentration of 10 to 200 µM, and (ii) uridine at a concentration of 1 to 10 mM.

3. The method of claim 1, wherein the culturing is batch culturing, fed-batch culturing, continuous culturing, or a combination thereof.

4. The method of claim 1, comprising:
(a) culturing the recombinant antibody-expressing CHO cells in a medium comprising glycerol at a concentration of 0.1 to 5% (v/v) and manganese at a concentration of 10 to 200 µM; and
(b) culturing the CHO cells cultured in step (a) in a medium further comprising uridine at a concentration of 1 to 10 mM.

5. The method of claim 4, wherein step (a) is performed for 3 days to 8 days.

6. The method of claim 4, further comprising a step (c) of culturing the CHO cells cultured in the step (b) by adding a feed medium comprising glycerol and manganese.

7. The method of claim 6, wherein the culturing in the step (c) is fed-batch culturing.

8. The method of claim 1 comprising:
(a) culturing the recombinant antibody-expressing CHO cells in a medium comprising glycerol at a concentration of 0.1 to 5% (v/v) and manganese at a concentration of 20 to 120 µM;
(b) culturing the CHO cells cultured in step (a) in a medium comprising uridine at a concentration of 3 to 10 mM; and
(c) culturing the CHO cells cultured in step (b) in fed-batch using a medium comprising glycerol and manganese.

9. The method of claim 1, wherein the sugar chain content of the antibody prepared by the method comprises a galactosylation content within the range of 35 to 50% and an afucosylation content within the range of 8 to 20%.

10. The method of claim 1, wherein the antibody is trastuzumab.

11. A method of regulating the sugar chain content of a recombinant antibody, the method comprising: culturing Chinese hamster ovary (CHO) cells expressing the recombinant antibody in a medium comprising: as additives, glycerol at a concentration of 0.1 to 5% (v/v) and either (i) manganese at a concentration of 20 to 120 µM or (ii) uridine at a concentration of 3 to 10 mM, or both (i) and (ii); wherein the regulated sugar chain content is a sugar chain content in which afucosylation is increased compared to the sugar chain content of the same antibody produced in the same medium not containing added glycerol.

12. The method of claim 11, comprising culturing the recombinant antibody-expressing CHO cells in a medium comprising glycerol at a concentration of 0.1 to 5% (v/v), and (i) manganese at a concentration of 20 to 120 µM, and (ii) uridine at a concentration of 3 to 10 mM.

* * * * *